US012558050B2

(12) United States Patent
Narasimha Murthy et al.

(10) Patent No.: US 12,558,050 B2
(45) Date of Patent: Feb. 24, 2026

(54) METHOD AND DEVICE FOR GENERATING A VESSEL IMAGING SEQUENCE

(71) Applicant: Siemens Healthineers AG, Forchheim (DE)

(72) Inventors: Venkatesh Narasimha Murthy, Hillsborough, NJ (US); Anamaria Vizitiu, Covasna (RO); Mehmet Akif Gulsun, Princeton, NJ (US); Sebastien Piat, Lawrence Township, NJ (US); Florin-Cristian Ghesu, Baiersdorf (DE)

(73) Assignee: Siemens Healthineers AG, Forchheim (DE)

( * ) Notice: Subject to any disclaimer, the term of this patent is extended or adjusted under 35 U.S.C. 154(b) by 294 days.

(21) Appl. No.: 18/535,044

(22) Filed: Dec. 11, 2023

(65) Prior Publication Data

US 2024/0260917 A1 Aug. 8, 2024

(30) Foreign Application Priority Data

Feb. 6, 2023 (EP) .................................... 23155127

(51) Int. Cl.
　　*A61B 6/50*　　　　(2024.01)
　　*A61B 5/0245*　　　(2006.01)
　　　　　　(Continued)

(52) U.S. Cl.
　　CPC ............ *A61B 6/504* (2013.01); *A61B 5/0245* (2013.01); *A61B 6/487* (2013.01); *G06T 7/0016* (2013.01);
　　　　　　(Continued)

(58) Field of Classification Search
None
See application file for complete search history.

(56) References Cited

U.S. PATENT DOCUMENTS 11,087,464 B2　　8/2021　Wagner et al.
2017/0238909 A1*　8/2017　Shin .................... A61B 5/7267
　　　　　　(Continued)

FOREIGN PATENT DOCUMENTS

EP　　　　4283561 A1　11/2023

OTHER PUBLICATIONS

"A Multi-Task Learning Framework for Fully Automated Assessment of Coronary Arteries in Angio Images" U.S. Appl. No. 17/934,213, filed Sep. 22, 2022.
　　　　　　(Continued)

*Primary Examiner* — Miya J Cato

(57) ABSTRACT

A vessel imaging sequence including plurality of vessel imaging frames and a corresponding ECG signal are generated by encoding, using a first encoder, an input vessel imaging sequence to generate a plurality of vessel latent space vectors, each vessel latent space vector corresponding to an input vessel imaging frame of the input vessel imaging sequence, encoding, using a second encoder, an input ECG signal to generate a plurality of ECG latent space vectors, decoding, using a first decoder, the plurality of vessel latent space vectors and the plurality of ECG latent space vectors to generate the vessel imaging sequence and decoding, using a second decoder, the vessel latent space vector and the ECG latent space vector to generate the ECG signal.

20 Claims, 11 Drawing Sheets

(51) Int. Cl.
    *A61B 6/00*         (2024.01)
    *G06T 7/00*         (2017.01)

(52) U.S. Cl.
    CPC ............... *G06T 2207/10121* (2013.01); *G06T 2207/20084* (2013.01); *G06T 2207/30101* (2013.01)

(56) References Cited

U.S. PATENT DOCUMENTS

| | | | |
|---|---|---|---|
| 2020/0222018 A1* | 7/2020 | van Walsum | A61B 6/5264 |
| 2022/0361834 A1 | 11/2022 | Butler et al. | |
| 2024/0342496 A1* | 10/2024 | Chon | G06N 3/045 |

OTHER PUBLICATIONS

Jeong Daehyeon et al: "Deep-Learning-Based Registration of Diagnostic Angiogram and Live Fluoroscopy for Percutaneous Coronary Intervention", IEEE Access, IEEE, USA, vol. 9, Jul. 20, 2021 (Jul. 20, 2021), pp. 103465-103480.

Ma, Hua, et al. "Dynamic coronary roadmapping via catheter tip tracking in X-ray fluoroscopy with deep learning based Bayesian filtering." Medical image analysis 61 (2020): 101634.

Piayda, Kerstin et al. "Dynamic coronary roadmapping during percutaneous coronary intervention: a feasibility study." European Journal of Medical Research 23 (2018).

Extended European Search Report (EESR) mailed May 26, 2023 in corresponding European Patent Application No. 23155127.6.

* cited by examiner

670

682

METHOD AND DEVICE FOR GENERATING A VESSEL IMAGING SEQUENCE

RELATED APPLICATION

This application claims the benefit of EP 23155127.6, filed on Feb. 6, 2023, which is hereby incorporated by reference in its entirety.

TECHNICAL FIELD

The present disclosure generally relates to imaging of vessels and more precisely to providing vessel imaging frames indicating vessel information with limited or no use of contrast medium.

BACKGROUND

Vessel imaging frames are typically recorded using, e.g., angiography or fluoroscopy, which expose a patient to radiation. In order for these vessel imaging frames to include sufficient vessel information, such as contrasted vessel trees or a position and trajectory of a catheter and its guidewire, typically requires recording vessel imaging frames over a number of cardiac cycles. Accordingly, the patient may be exposed to radiation for an extended period of time. Further, at least during angiography, contrast medium needs to be applied into the vessels of the patient. Since contrast medium needs to be radio-opaque, contrast medium may include iodine or other substances, which may be detrimental to the renal function of the patient. Accordingly, prolonged contrast medium application during recoding of vessel imaging frames may cause health issues for the patient.

Therefore, it is an objective to reduce the recoding time of vessel imaging frames and the use of contrast medium, if applied, while ensuring that the frames include sufficient vessel information.

SUMMARY

To achieve this objective, a method is provided for generating a vessel imaging sequence comprising a plurality of vessel imaging frames and a corresponding electrocardiogram (ECG) signal. The method includes obtaining an input vessel imaging sequence including a plurality of input vessel imaging frames and a corresponding input ECG signal, encoding, using a first encoder, the input vessel imaging sequence to generate a plurality of vessel latent space vectors, each vessel latent space vector corresponding to an input vessel imaging frame of the input vessel imaging sequence, encoding, using a second encoder, the ECG signal to generate a plurality of ECG latent space vectors, decoding, using a first decoder, the plurality of vessel latent space vectors and the plurality of ECG latent space vectors to generate the vessel imaging sequence; and decoding, using a second decoder, the vessel latent space vector and the ECG latent space vector to generate the ECG signal.

To further achieve this objective, a vessel imaging sequence generation device is provided. The vessel imaging sequence including a plurality of vessel imaging frames, including at least one processor and a storage medium including machine-readable instructions. The machine-readable instructions cause the at least one processor to obtain an input vessel imaging sequence including a plurality of in-put vessel imaging frames and a corresponding input ECG signal, encode, using a first encoder, the input vessel imaging sequence to generate a plurality of vessel latent space vectors, each vessel latent space vector corresponding to an input vessel imaging of the input vessel imaging sequence, encode, using a second encoder, the ECG signal to generate a plurality of ECG latent space vectors, decode, using a first decoder, the plurality of vessel latent space vectors and the plurality of ECG latent space vectors to generate the vessel imaging sequence and decode, using a second decoder, the vessel latent space vector and the ECG latent space vector to generate the ECG signal.

BRIEF DESCRIPTION OF THE DRAWINGS

Examples of the present disclosure will be described with reference to the following appended drawings, in which like reference signs refer to like elements.

It should be understood that the above-identified drawings are in no way meant to limit the scope of the present disclosure. Rather, these drawings are provided to assist in understanding the present disclosure. The person skilled in the art will readily understand that aspects of the present disclosure shown in one drawing may be combined with aspects in another drawing or may be omitted without departing from the scope of the present disclosure.

DETAILED DESCRIPTION

A method and device are provided for generating a vessel imaging sequence and a corresponding ECG signal. To generate the vessel imaging sequence, an input vessel imaging sequence, such as an input vessel image sequence, a vessel segmentation sequence, or a fluoroscopic imaging sequence, is encoded to generate vessel latent space vectors for each vessel imaging frame. The vessel latent space vectors collectively form a vessel latent space. Likewise, an input ECG signal is encoded to generate ECG latent space vectors, which may for example respectively correspond to one ECG measurement at a given ECG sampling point. The ECG latent space vectors collectively form an ECG latent space. Both the vessel latent space and the ECG latent space are then combined to form a combined or modified latent space. The modified latent space is then decoded twice, i.e., once to generate the vessel imaging sequence and once to generate the ECG signal corresponding to the vessel imaging sequence.

Figure 1:
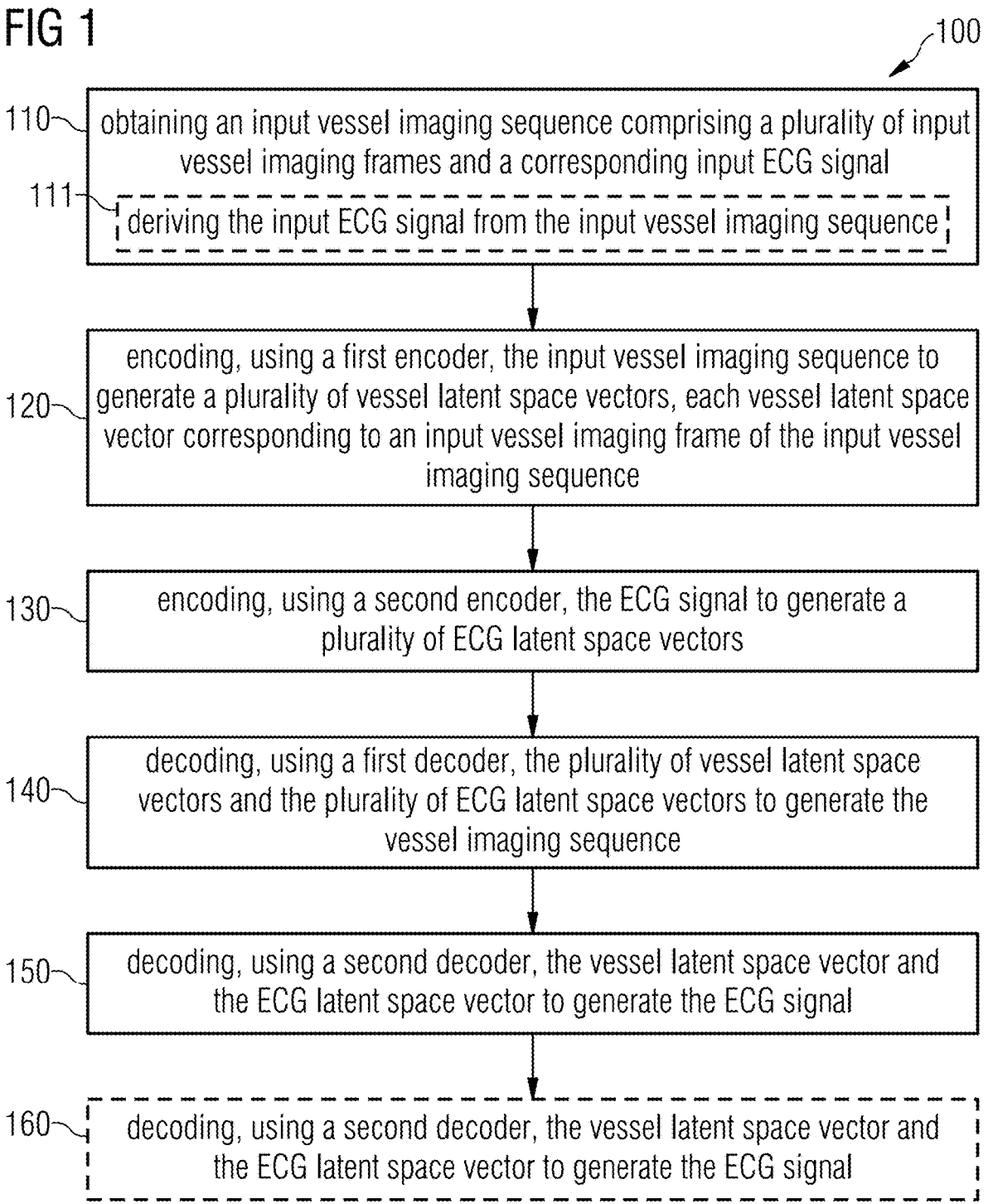
FIG. 1 provides a flowchart of a method for generating a vessel imaging sequence according to examples of the present disclosure.
Figure 2:
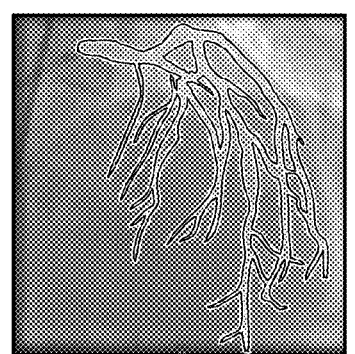
FIG. 2 illustrates example input vessel imaging frames according to examples of the present disclosure.
Figure 2:
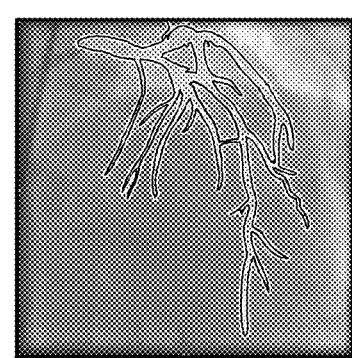
Figure 2:
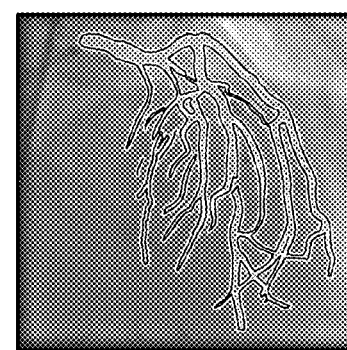
Figure 3:
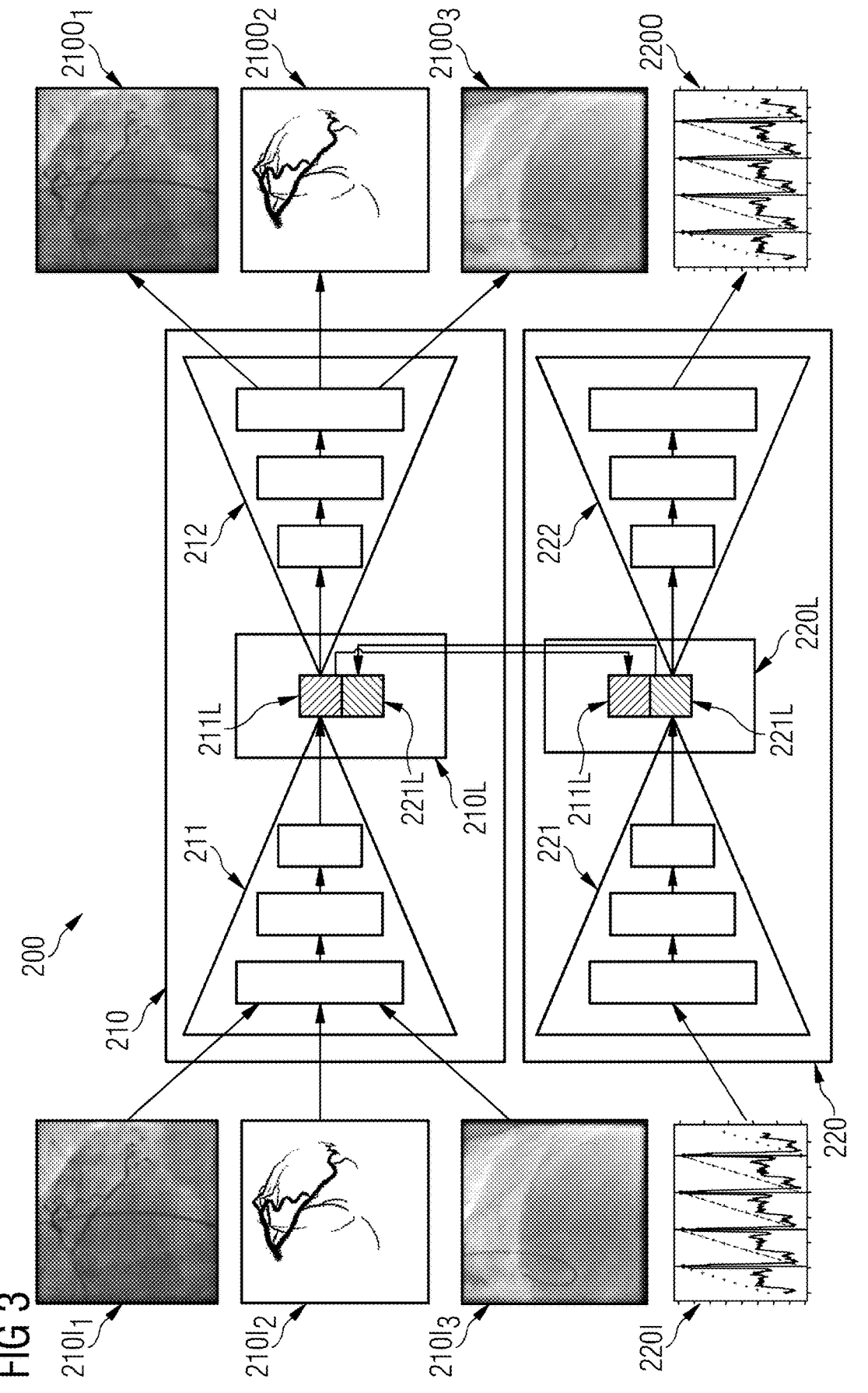
FIG. 3 illustrates a system implementing the method of FIG. 1 according to examples of the present disclosure.
Figure 10A:
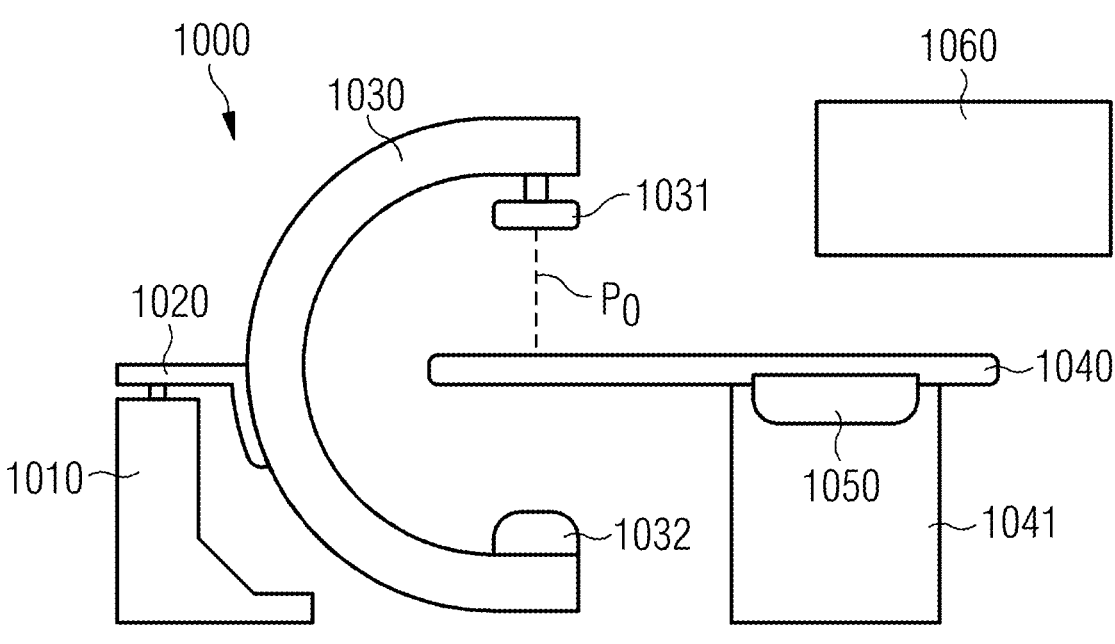
FIGS. 10A and 10B show an exemplary medical imaging system.
Figure 10B:
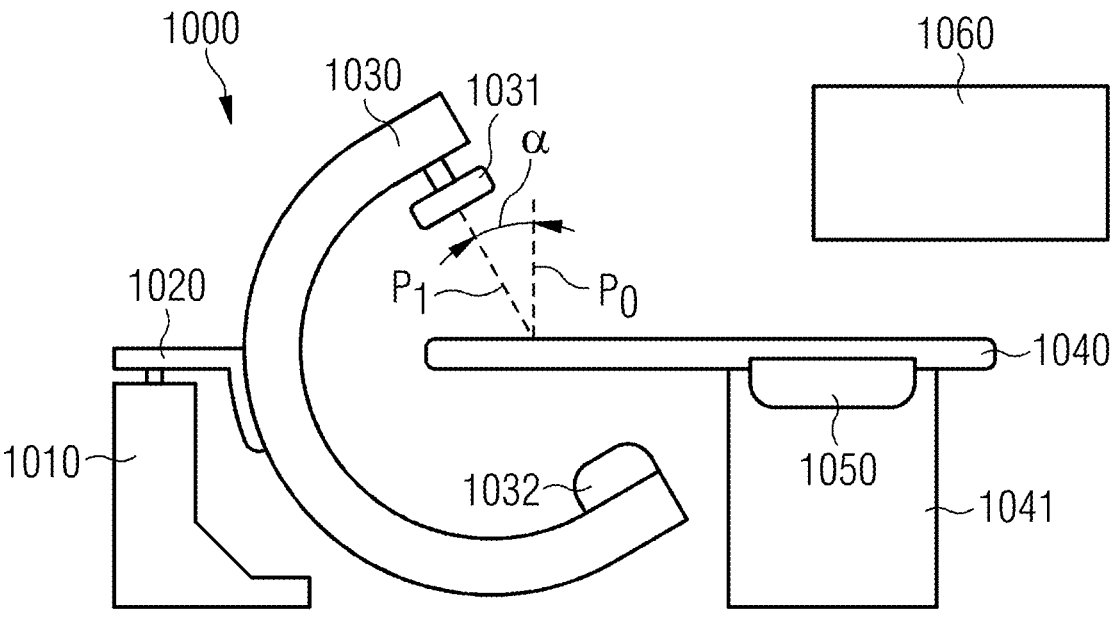
Figure 11:
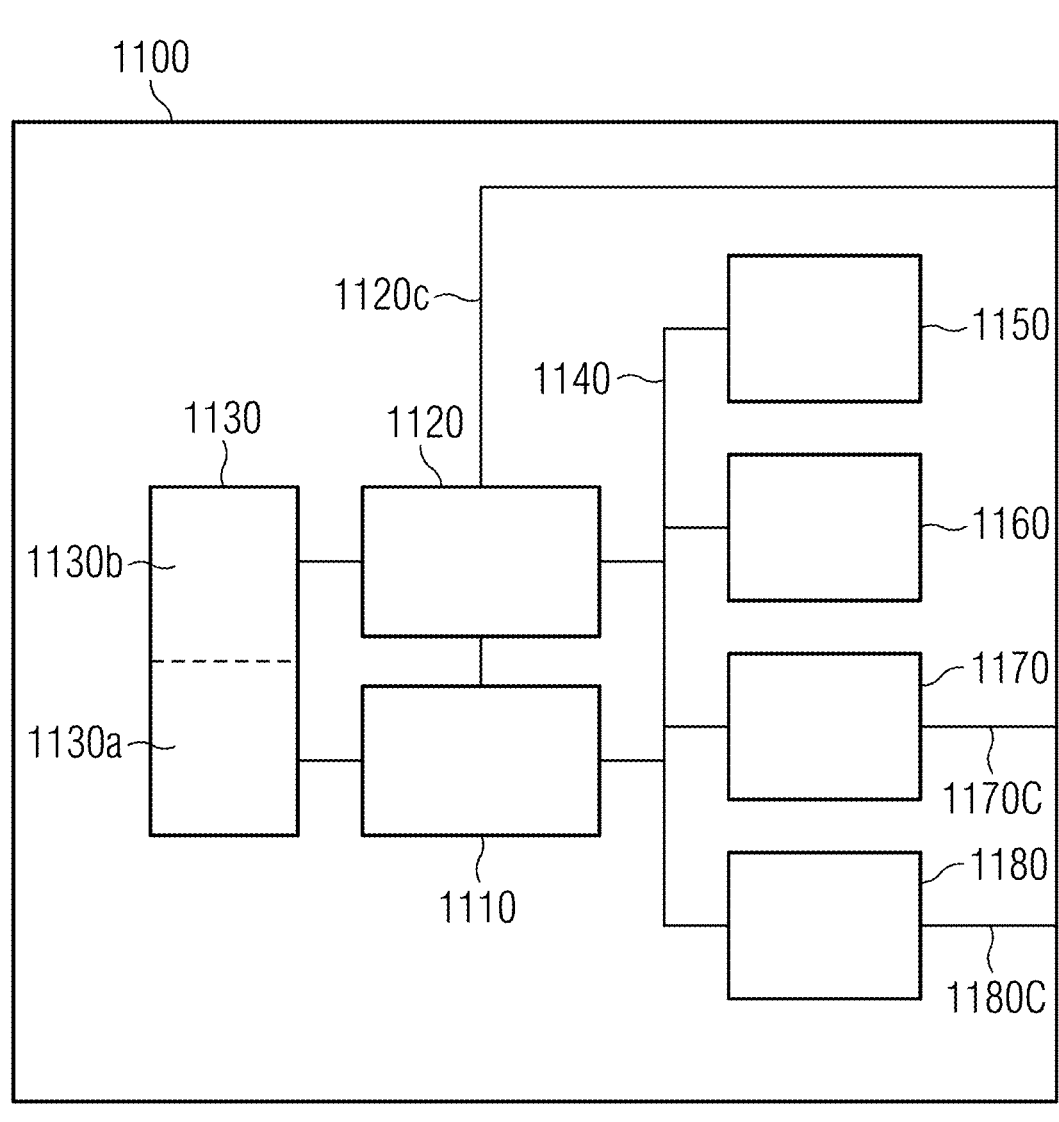
FIG. 11 shows an exemplary computing device.

This general concept will now be explained with reference to the appended drawings. FIG. 1 illustrates a flowchart of the method for generating a vessel imaging sequence, while FIG. 2 illustrates example input vessel imaging frames, and FIG. 3 illustrates a system implementing the method for generating the vessel imaging sequence. FIGS. 6A to 9 illustrate a vessel imaging workflow employing the method for generating a vessel imaging sequence. Finally, FIGS. 10 and 11 illustrate devices relating to aspects and the implementation of the method for generating a vessel imaging sequence.

FIG. 1 illustrates a flowchart of a method 100 for generating a vessel imaging sequence and a corresponding ECG signal. Optional acts of method 100 are indicated in FIG. 1 as dashed boxes. Sub acts of acts of method 100 are indicated as boxes inside the boxes of their corresponding acts.

The vessel imaging sequence includes a plurality of vessel imaging frames, which may e.g., be vessel image frames obtained using angiography, vessel segmentation frames, i.e., frames corresponding to an output of a vessel segmentation process performed on the vessel image frames, or fluoroscopic image frames. In other words, the vessel imaging frames may be frames that indicate the course of vessels, such as arteries, veins or lymphatic vessels, either based on a contrast-medium or based on vessel segmentation performed using vessel imaging frames indicating a presence of contrast medium. The vessel imaging frames may be frames that indicate a position of a catheter, a guidewire of the catheter or both. Based on the indicated position of the catheter, the guidewire or both within such vessel imaging frames, these vessel imaging frames may likewise indicate the course of vessels. In other words, fluoroscopic image frames may indicate the course of vessels without contrast medium. Examples of vessel image frames, input vessel segmentation frames and fluoroscopic frames are provided in FIG. 3 by input frames $210O_1$, $210O_2$, and $210O_3$, respectively.

The ECG signal corresponding to the vessel imaging frames provides a signal indicative of the cardiac action potential of the heart, as e.g., measured with a 12-lead ECG. Accordingly, the ECG signal may provide, for each sampling time, twelve values corresponding to twelve measurements of the cardiac action potential of the heart at twelve different angles. It will be understood, however, that other types of ECG may be used, and that accordingly, the ECG signal may include more or fewer values per sampling time. Accordingly, the ECG signal may e.g., be considered as a plurality of ECG measurement vectors, wherein the number of ECG measurement vectors in the plurality corresponds to the number of sampling times. Each sampling time corresponds to a sampling time of a vessel imaging frame, i.e., a point in time within a cardiac cycle to which the frame corresponds. For example, if a cardiac cycle is sampled 30 times, the vessel imaging sequence includes 30 vessel imaging frames and the ECG signal includes 30 corresponding ECG measurement vectors.

In act 110, method 100 obtains an input vessel imaging sequence including a plurality of input vessel imaging frames and a corresponding input ECG signal.

It will be understood that method 100 may in act 110, record the input vessel imaging sequence and the input ECG signal or may receive, e.g., on a storage medium or wirelessly, the input vessel sequence and the input ECG signal.

Obtaining in the context of the present disclosure is thus to be construed as recording and/or receiving the input vessel imaging sequence and the corresponding input ECG.

The input vessel imaging sequence includes a plurality of input vessel imaging frames, which may e.g., be input vessel image frames recorded using angiography, such as processed or unprocessed x-ray detector values, input vessel segmentation frames, i.e., frames corresponding to an output of a vessel segmentation process performed on the vessel image frames, or input fluoroscopic image frames recorded using fluoroscopy. Examples of vessel image frames are shown in FIG. 2. Examples of input vessel image frames, input vessel segmentation frames, and fluoroscopic frames are provided in FIG. 3 by input frames $210I_1$, $210I_2$ and $210I_3$, respectively. Accordingly, the input vessel imaging sequence may be one of an input vessel image sequence, an input vessel segmentation sequence derived from the input vessel image sequence, and a fluoroscopic imaging sequence. The input vessel imaging sequence may be obtained during a single cardiac cycle, as will be discussed in more detail with regard to the subsequent acts of method 100.

Like the vessel imaging sequence, the input vessel imaging sequence indicates the course of vessels. However, the input vessel imaging sequence may not fully indicate the course of the vessels. This may be due to the circulation of contrast medium in the vessels during angiography, leading to the vessels being only partially visible in e.g., the input vessel image frames or the corresponding input vessel segmentation frames of the input vessel imaging frames. This is illustrated in FIG. 2, which shows three exemplary input vessel imaging frames, in which a vessel tree is shown. In each of the three exemplary input vessel images, the vessel tree appears differently due to the circulation of the contrast medium in the vessel tree. Further, the number of sampling times of the input vessel imaging sequence, i.e., the temporal resolution of the input vessel imaging sequence, is lower than the number of sampling times of the vessel imaging sequence, i.e., the temporal resolution of the vessel imaging sequence. That is, the frame rate of the input vessel imaging sequence may be lower than the frame rate of the vessel imaging sequence. For example, the frame rate of the input vessel imaging sequence may be in a range of 7 to 15 frames per second while the frame rate of the vessel imaging sequence may be in a range of 15 to 30 frames per second. The lower temporal resolution of the input vessel imaging sequence may likewise lead to the input vessel imaging sequence to not fully indicate the course of the vessels, e.g., due to the circulation of contrast medium through certain vessel branches or by showing the movement of the catheter, the guidewire, or both in intervals with a size leading to uncertainty regarding the course of the vessel during the intervals.

The input ECG signal corresponds to the ECG signal discussed above. Accordingly, the input ECG signal may be considered as a plurality of input ECG measurement vectors, wherein the number of input ECG measurement vectors in the plurality corresponds to the number of sampling times. However, like the input vessel imaging sequence compared to the vessel imaging sequence, the temporal resolution, i.e., the number of sampling times, of the input ECG signal is lower than the temporal resolution of the ECG signal. Accordingly, the input ECG signal may not render visible ECG measurement information of some parts of the cardiac cycle. An example of an input ECG signal is for example shown in FIG. 3, which illustrates input ECG signal 2201.

Act 110 may include an act 111, in which method 100 derives the input ECG signal from the input vessel imaging sequence. In other words, method 100 may not directly obtain the input ECG signal but may derive the input ECG signal at respective sampling times based on the respective input vessel imaging frames. Method 100 may derive the input ECG signal e.g., by analyzing the changes of the course of the vessels or the change of the position of a catheter tip shown in the respective input vessel imaging frames since these changes are at least in part caused by cardiac motion. In other words, method 100 may in act 111 analyze these changes to determine the cardiac motion occurring between input vessel imaging frames and may then, based on the determined cardiac motion, determine the ECG signal at the sampling time of the input vessel imaging frame.

As will become apparent by the discussion of the subsequent acts of the method 100, method 100 derives the vessel imaging sequence from the input vessel imaging sequence by increasing the temporal resolution compared to the input vessel imaging sequence. This increase in temporal resolution starting from the input vessel imaging sequence extracts the indication of the course of the vessel not visible in the input vessel imaging frames based on their temporal relationship and renders them visible in the vessel imaging sequence generated by method 100. The same applies to the ECG signal and the input ECG signal.

In act 120, method 100 encodes, using a first encoder, the input vessel imaging sequence to generate a plurality of vessel latent space vectors. Each vessel latent space vector corresponds to an input vessel imaging frame of the input vessel imaging sequence. In other words, method 100 converts each input vessel imaging frame into a latent space vector, i.e., a vector in a latent space. The latent space represents aspects of input vessel imaging frames, which indicate, if present in an input vessel imaging frame, the presence of a vessel indication, such as a vessel, a vessel segment, a catheter or a guidewire at a given position in the respective vessel image frame. Each element of a vessel latent space vector thus provides a weight of the vessel indications within an input vessel imaging frame. To determine the vessel indications and thereby defining the latent space, the first encoder is trained with example input vessel imaging frames. The first encoder may for example be a convolutional neural network, a principal component analysis or a transformer-based neural network architecture. Accordingly, the latent space may be defined by the elements of the last layer of the convolutional neural network or the number of principal components, i.e., orthogonal unit vectors, determined by the principal component analysis, each respectively trained on example input vessel imaging frames. In these cases, the respective vessel latent space vectors may respectively be activations of the elements of the last layer or weightings of the unit vectors.

In act 130, method 100 encodes, using a second encoder, the input ECG signal to generate a plurality of ECG latent space vectors. Each ECG latent space vector corresponds to an input ECG measurement vector. However, while the ECG measurement vector indicates the measurement of cardiac action potentials measured at various angles, the ECG latent space vector indicates a weight of features of the ECG measurements indicative of the cardiac cycle, as defined by an ECG latent space. Accordingly, the ECG latent space defines the features of the ECG measurements indicative of the cardiac cycle. To determine the ECG latent space, the second encoder is trained with example input ECG signals to identify the features of the ECG measurements indicative of the cardiac cycle. Like the first encoder, the second encoder may thus be a convolutional neural network, a principal component analysis or a transformer-based neural network architecture. The latent space may be defined accordingly, leading to ECG latent space vectors defining e.g., activations of the elements of the last layer or weightings of the unit vectors.

In both act 120 and 130, the input vessel imaging frames and the input ECG signal may be used to respectively further train the first encoder and the second encoder.

In act 140, method 100 decodes, using a first decoder, the plurality of vessel latent space vectors and the plurality of ECG latent space vectors to generate the vessel imaging sequence. In other words, the first decoder receives the plurality of vessel latent space vectors and the plurality of ECG latent space vectors as input and generates the vessel imaging sequence based on this input.

As discussed above, the vessel latent space vectors provide a weight of the vessel indications within an input vessel imaging frame and the ECG latent space vectors provide a weight of features of the ECG measurements indicative of the cardiac cycle. In act 140, method 100 takes both latent space vectors and generates the vessel imaging sequence based thereon. To achieve a higher temporal resolution of the vessel imaging sequence compared to the input vessel imaging sequence, method 100, as part of act 140, interpolates between the vessel latent space vectors while using the ECG latent space vectors as guidance of the interpolation. For example, the vessel latent space vectors may be used to determine an interpolation weight between vessel latent space vectors or may be used to otherwise inform the interpolation of the vessel latent space vectors. The accordingly interpolated vessel latent space vectors are then used by the first decoder to generate the vessel imaging sequence by reconstructing the vessel imaging frames from the interpolated vessel latent space vectors. The first decoder may thus be a convolutional neural network, a principal component analysis or a transformer-based neural network architecture, like the first encoder and the second encoder. As will be understood, to enable reconstruction of the vessel image frames, the architecture of the first decoder corresponds to the first encoder.

In act 150, method 100 decodes, using a second decoder, the vessel latent space vector and the ECG latent space vector to generate the ECG signal. In other words, the second decoder receives the plurality of vessel latent space vectors and the plurality of ECG latent space vectors as input and generates the vessel imaging sequence based on this input.

Similar to act 140, method 100 in act 150 takes both pluralities of latent space vectors and generates the ECG signal based on both pluralities of latent space vectors. While in act 140, the ECG latent space vectors served as guidance for the interpolation of the vessel latent space vectors, in act 150 the vessel latent space vectors serve as guidance for the interpolation of the ECG latent space vectors. Thus, to achieve a higher temporal resolution of the ECG signal compared to the input ECG signal, the second decoder interpolates the ECG latent space vectors based, e.g., on an interpolation weight or otherwise informed by the vessel latent space vectors. The accordingly interpolated ECG latent space vectors are then used by the second decoder to generate the ECG signal by reconstructing the ECG measurement values at each interpolated sampling time from the interpolated vessel latent space vectors. The second decoder may thus be a convolutional neural network, a principal component analysis or a transformer-based neural network architecture, like the previously discussed encoders and decoders. As will be understood, to enable reconstruction of the vessel image frames, the architecture of the second decoder corresponds to the second encoder.

By generating both the vessel image sequence and the ECG signal based on the vessel latent space vectors and the ECG latent space vectors, recording the input vessel imaging sequence during only a single cardiac cycle is sufficient since all information can be extrapolated due to the two pluralities of latent space vectors. This is in contrast to other vessel imaging sequence generations, in particular manual vessel imaging sequence generations, which require recording the input vessel imaging sequence for multiple cardiac cycles, leading to an increased radiation exposure and, if contrast medium is used, also to an increased risk for the renal function of the patient. Accordingly, by generating both the vessel image sequence and the ECG signal based on the vessel latent space vectors and the ECG latent space vectors, method 100 provides a vessel imaging sequence having a high temporal resolution while reducing the radiation exposure and the exposure to contrast medium, if applied.

To enable act 140 and act 150, the plurality of vessel latent space vectors and the plurality of ECG latent space vectors may respectively be configured to enable a reconstruction of the input vessel imaging sequence and of the input ECG signal. Further, both the first encoder and the first decoder may be considered as forming a first modified latent space autoencoder due to the plurality of vessel latent space vectors and the plurality of ECG latent space vectors effectively forming a modified latent space due to their combination. Likewise, the second encoder and the second decoder may be considered as forming a second modified latent space autoencoder.

Method 100 may further include an act 160, in which method 100 may derive at least one of a respiratory motion model and a cardiac motion model from the plurality of vessel latent space vectors and the plurality of ECG latent space vectors. The respiratory motion model and a cardiac motion model may be derived based on changes between adjacent vessel latent space vectors and adjacent ECG latent space vectors, respectively. Adjacent in this context refers to being adjacent in time, e.g., corresponding to adjacent sampling times. The respiratory motion model and a cardiac motion model can be respectively derived from the plurality of vessel latent space vectors and the plurality of ECG latent space vectors since the changes between adjacent vessel latent space vectors and adjacent plurality of ECG latent space vectors are caused by the breathing motion and the cardiac motion of the vessels.

To further improve the generation the vessel imaging sequence, the first encoder and the second encoder may also be trained with the vessel imaging sequence following its generation.

It will be understood that method 100 may be performed at any angiography angle or fluoroscopy angle and for any number such angles. Briefly referring to FIGS. 10A and 10B, both show a medical imaging system 1000 including a rotatable C-arm 1030. X-ray emitter 1031 and X-ray detector 1032 may be mounted on C-arm 1030. In FIG. 10A, C-arm 1030 is in a neutral position $P_0$, i.e., X-ray emitter 1031 are located directly above a patient surface 1040. In FIG. 10B, C-arm 1030 and thereby X-ray emitter 1031 are rotated counter-clockwise with respect to neutral position $P_0$ of C-arm 1030 in FIG. 10A to a position $P_1$. The angle between position $P_0$ and position $P_1$, as indicated in FIG. 10B, is referred to as the angiography angle or the fluoroscopy angle, depending on the medical imaging process. It will be understood that the neutral position may be used as an imaging position. In such a case, the angiography angle is 0°. Further, in case of a single axis angiography system, the neutral position is typically defined as shown in FIG. 10A. In multiple axis angiography systems, additional C-arms may be present, such as a ceiling mounted C-arm. In such a case, the neutral position may be defined as the position in which X-ray emitter 1031 and X-ray detector 1032 are at the same level as a patient on patient surface 1040.

While the above definition of the angiography angle is based on the position of X-ray emitter 1031, the angiography angle may analogously be defined based on the position of X-ray detector 1032.

FIG. 3 illustrates a system 200 implementing method 100. System 200 may include a first modified latent-space autoencoder 210 and a second modified latent-space autoencoder 220.

First modified latent space autoencoder 210 includes a first encoder 211 and a first decoder 212. First encoder 211 is configured to generate the vessel latent space vectors discussed above based on receiving the input vessel imaging sequence. First encoder 211 may thus implement act 120 of method 100. The input vessel imaging sequence is illustrated by exemplary input vessel image frame $210I_1$, exemplary input vessel segmentation frame $210I_2$ and exemplary input fluoroscopic frame $210I_3$. The vessel latent space vectors are illustrated in FIG. 3 by vessel latent space vectors 211L. Vessel latent space vectors 211L and ECG latent space vectors 221L are provided to first decoder 212 to generate the vessel imaging sequence, illustrated in FIG. 3 by exemplary vessel image frame $210O_1$, exemplary vessel segmentation frame $210O_2$ and exemplary fluoroscopic frame $210O_3$. First decoder 212 may thus implement act 140 of method 100. Vessel latent space vectors 211L and ECG latent space vectors 221L may be considered as a modified latent space 210L, as indicated by the box around vessel latent space vectors 211L and ECG latent space vectors 221L.

Second modified latent space autoencoder 220 includes a second encoder 221 and a second decoder 222. Second encoder 221 is configured to generate the ECG latent space vectors discussed above based on receiving the input ECG signal. Second encoder 221 may thus implement act 130 of method 100. The input ECG sequence is illustrated by exemplary ECG input signal 220I. The ECG latent space vectors are illustrated in FIG. 3 by vessel latent space vectors 221L. ECG latent space vectors 221L and vessel latent space vectors 211L are provided to second decoder 222 to generate the ECG signal, illustrated in FIG. 3 by exemplary ECG signal 220O. Second decoder 222 may thus implement act 150 of method 100. ECG latent space vectors 221L and vessel latent space vectors 211L may be considered as a modified latent space 220L, as indicated by the box around ECG latent space vectors 221L and vessel latent space vectors 211L.

As will be discussed in the following, method 100 and system 200 may be employed in a vessel imaging workflow, which will be discussed in the following.

Figures 4, 4A:
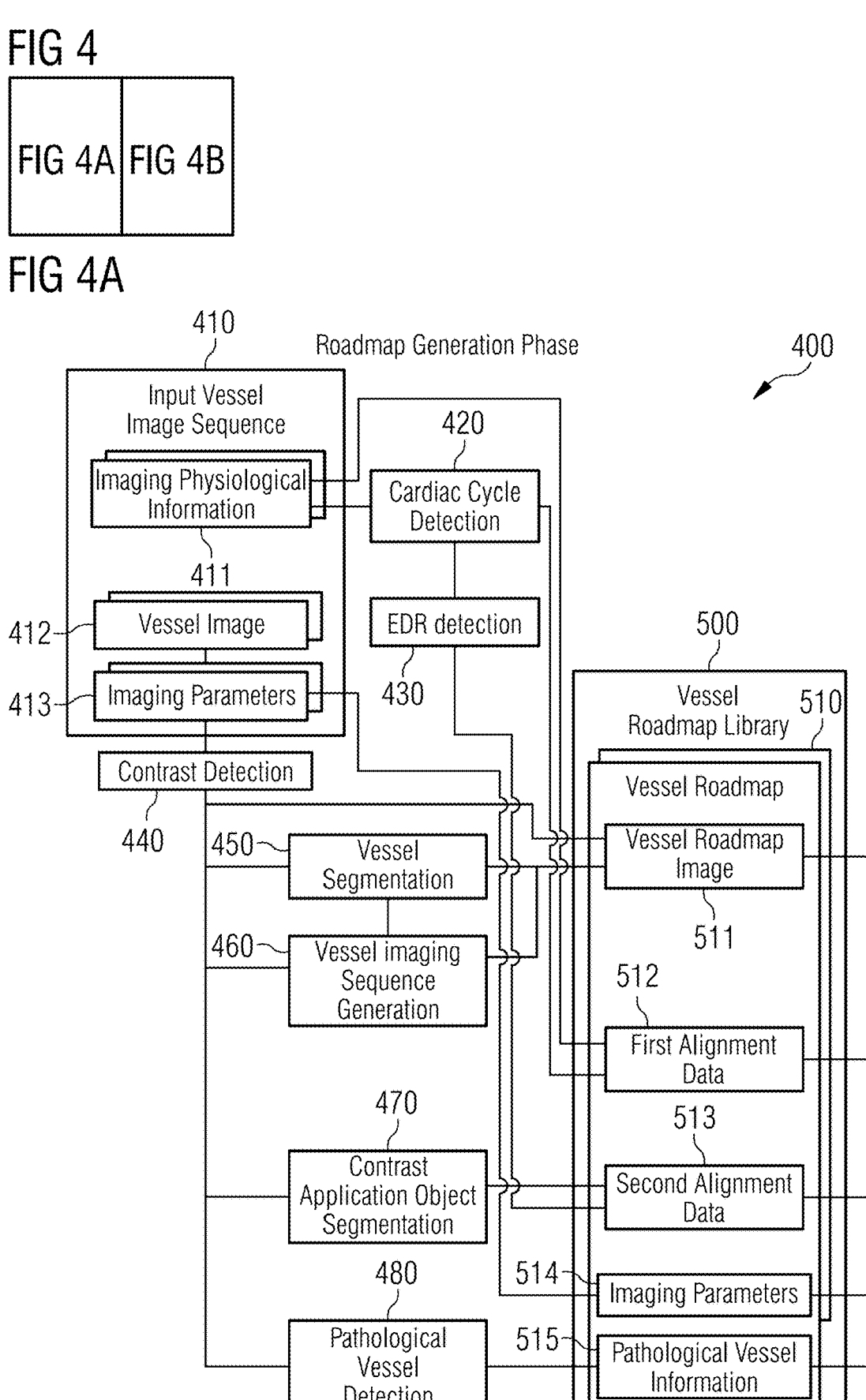
FIGS. 4, 4A and 4B show a schematic diagram of a vessel imaging workflow, which employs the method of FIG. 1 according to examples of the present disclosure.
Figure 4B:
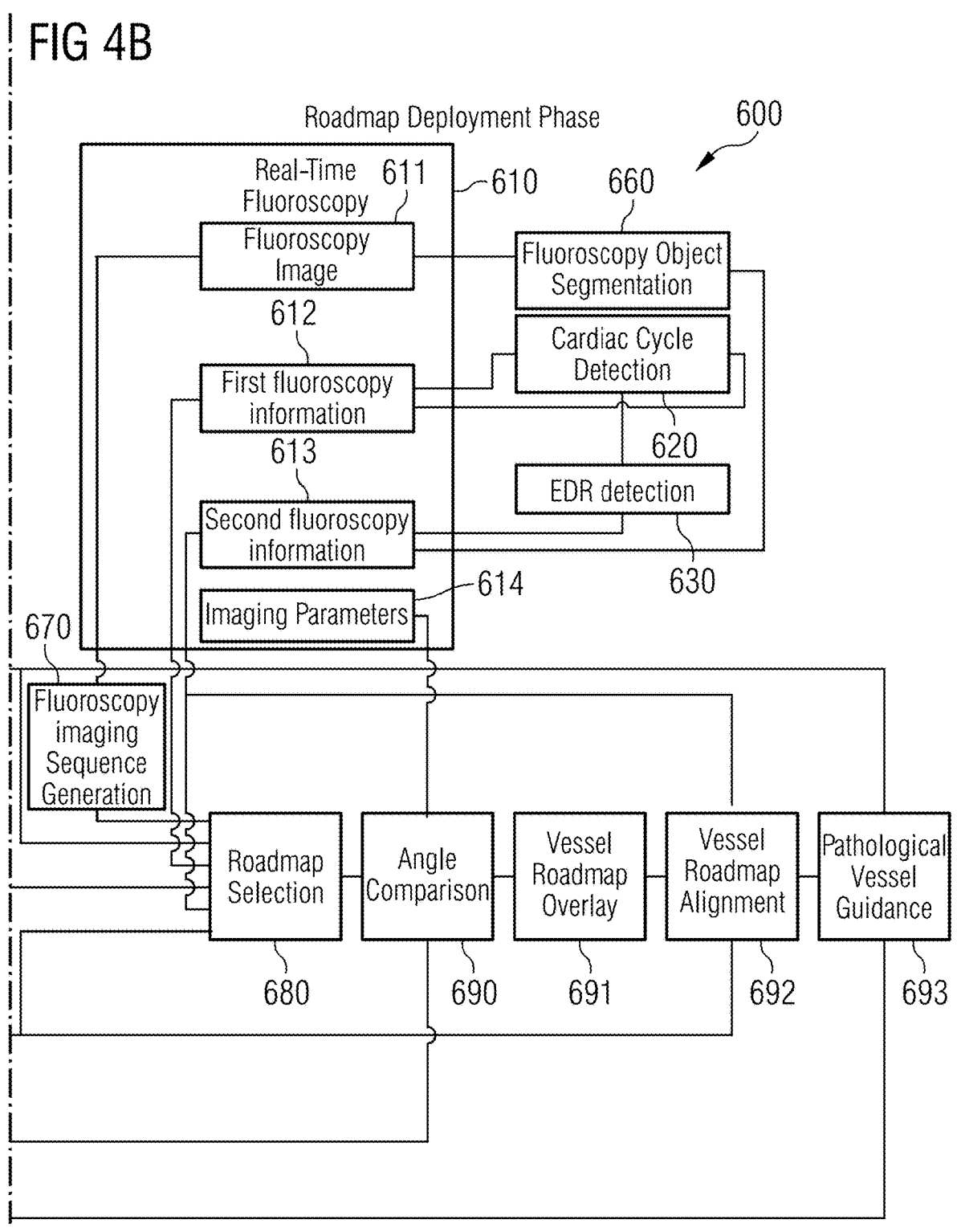

FIGS. 4, 4A and 4B show a schematic diagram of a vessel imaging workflow. FIG. 4 shows the orientation of FIGS. 4A and 4B with regard to one another. The lines shown in FIGS. 4A and 4B indicate where various data, such as vessel image 412 or the output of processing entities, such as vessel segmentation 450, is routed. The blocks shown in FIG. 4 indicate both processing entities, such as cardiac cycle detection 420, and stored data elements, such as vessel roadmap 510.

The workflow is separated into two phases, i.e., a roadmap generation phase 400 and a roadmap deployment phase 600. Roadmap generation phase 400 is shown in FIG. 4A. Roadmap deployment phase 600 is shown in FIG. 4B. During roadmap generation phase 400, a vessel image sequence 410 is processed to generate a vessel roadmap library 600. Vessel roadmap library 500 is then deployed in roadmap deployment phase 600 to provide a dynamic vessel roadmap for guidance of a fluoroscopy object during fluoroscopy. First, roadmap generation phase 400 will be described.

Input vessel image sequence 410 may include a plurality of vessel images 412, which corresponds to the input vessel image frames discussed above. In some examples of the present disclosure, vessel images 412 may be stored as or may be Digital Imaging and Communications in Medicine (DICOM) images.

Vessel image sequence 410 may include imaging physiological information 411. Imaging physiological information 411 may be any physiological information of a patient recorded while the imaging method used to obtain vessel images 412 is performed and which may be used to later overlay and align vessel roadmaps with a real-time fluoroscopy image. In particular, imaging physiological information 411 may be recorded at approximately the same point in time as the corresponding vessel image 412. In some embodiments, imaging physiological information 411 may include or may be an electrocardiogram (ECG) recorded while the imaging method used to obtain vessel images 412 is performed. In some embodiments, imaging physiological information may be stored as or may be a DICOM data tag included in the DICOM image file of the corresponding vessel image 412. Imaging physiological information 411 may be included in, e.g., stored as part of, first alignment data 812 of a vessel roadmap 610.

Input vessel image sequence 410 may include imaging information 413. Imaging information 413 may indicate one or more parameters associated with an imaging method used to obtain vessel image frames 412. As discussed above, the imaging method used to obtain vessel image frames 412 may for example be angiography. Accordingly, imaging information 413 may include at least one of an angiography angle and a contrast medium dosage.

The contrast medium dosage may indicate the dosage of radio-opaque contrast medium administered to a patient to render the vessels of the patient visible during the imaging method. The contrast medium dosage may be measured in milliliters per kilogram of body weight. In the case of contrast media including iodine, the contrast medium dosage may also be measured in milligram iodine per kilogram of body weight.

Vessel images 412 may be processed by contrast detection 440 to detect contrasted vessel images among the plurality of vessel images 412. Contrast detection 440 may detect contrasted vessel images by detecting the presence of contrast medium in vessel images 412. Contrast detection 440 may in some examples of the present disclosure analyze the pixels of each vessel image frame 412 to detect, based on a property of the pixels, the presence of contrast medium in the respective vessel image 412. The property of the pixels may e.g., a brightness value or a color value. In some embodiments, a vessel image 412 may be identified as a contrasted vessel image if a single pixel indicative of contrast medium is identified. In some embodiments, a vessel image 412 may be identified as a contrasted vessel image if a number of pixels indicative of contrast medium which exceeds a contrast medium detection threshold is identified. In some embodiments, contrast detection 440 may detect contrasted vessel images among the plurality of vessel images using a deep learning model, such as Deep-Net, which identifies contrast medium in the vessel images 412 and provides a frame-by-frame classification of the input vessel image sequence 410. The contrasted vessel images detected by contrast detection 440 are then provided to vessel segmentation 450 and vessel imaging sequence generation 460. Furthermore, each contrasted vessel image may be included in, e.g., stored as part of, a vessel roadmap image 511 of vessel roadmap 510.

In some examples of the present disclosure, contrast detection 440 may also take into account the contrast medium dosage indicated by imaging parameters 413.

The contrasted vessel images detected by contrast detection 440 are provided to vessel segmentation 450, vessel imaging sequence generation 460 contrast application segmentation 470 and pathological vessel detection 480. Furthermore, each contrasted vessel image may be included in, e.g., stored as part of, a vessel roadmap image 411 of vessel roadmap 410.

Vessel segmentation 450 may perform vessel segmentation on the contrasted vessel images to generate vessel segmentation data, i.e., vessel segmentation frames. Accordingly, vessel segmentation 450 may generate data indicative of the position and/or the course of the vessels within the contrasted vessel images. Vessel segmentation data may be generated by vessel generation 450 based on a variety of image segmentation approaches, such as based on convolutional neural networks (CNN), e.g., U-Net, densely connected neural networks, deep-learning methods, graph-partitioning methods, e.g., Markoff random fields (MRF), or region-growing methods, e.g., split-and-merge segmentation. The vessel segmentation data may then be included in, e.g., stored as part of, a vessel roadmap image 511 of a vessel roadmap 510.

It should be noted that, while vessel segmentation 450 is shown in FIG. 4A as processing contrasted vessel image frames, vessel segmentation may also directly process vessel images frames 412 to generate vessel segmentation data prior to detecting contrasted vessel images. In some embodiments, vessel segmentation 450 may also be incorporated into or be part of contrast detection 440. In such embodiments, detecting pixels indicative of contrast mediums may at the same time be used to generate vessel segmentation data.

Vessel imaging sequence generation 460 may be implemented by method 100 of FIG. 1 and may thus increase the temporal resolution of input vessel image frames 412 by generating vessel roadmap image frames, i.e., vessel roadmap images 511 based on input vessel image frames.

Contrast application object segmentation 470 may perform contrast application object segmentation on the contrasted vessel images to generate contrast application object segmentation data. Accordingly, contrast application object segmentation data may identify a position and/or the course of the contrast application object in the contrasted vessel images. More precisely, the contrast application object segmentation data may in some embodiments be a catheter, which is used to apply the contrast medium. In other words, contrast application object segmentation 460 may for example detect a tip of a catheter and. The contrast application object segmentation data, i.e., e.g., the valid detected position of the tip of the catheter, may then be included in, e.g., stored as part of, second alignment data 513 of vessel roadmap 510.

While contrast application object segmentation 470 is shown in FIG. 4A as processing contrasted vessel images, contrast application object segmentation 460 may also directly process vessel images 412, e.g., based on act 111a of method 100.

Figure 5:
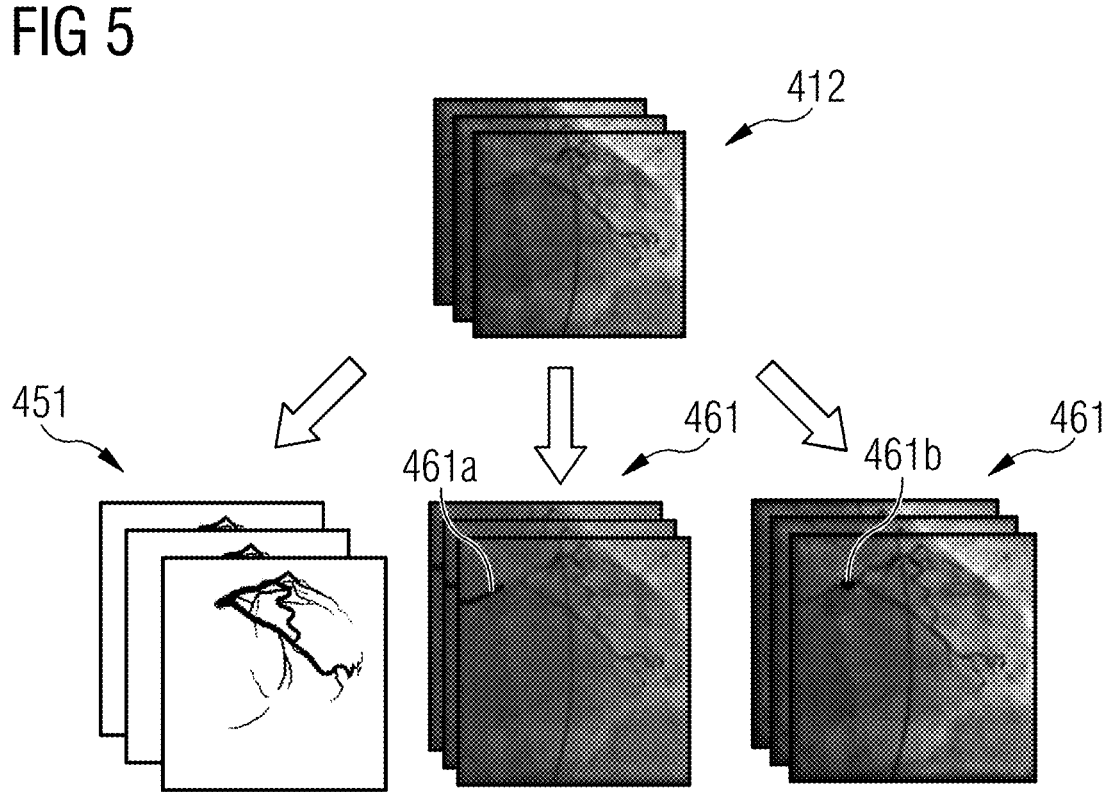
FIG. 5 shows examples of segmentations which may be obtained from a vessel image sequence according to examples of the present disclosure.

Both vessel segmentation 450 and contrast application object segmentation 460 perform image segmentation on vessel images 412 or contrasted vessel images, respectively. To better illustrate possible segmentations performed on vessel images 412 or contrasted vessel images, respectively, FIG. 5 shows three example segmentations of a vessel image 412. From left to right, FIG. 5 shows an example of vessel segmentation data 451 and two examples of contrast application object segmentation data 461. As can be seen, vessel segmentation data 451 indicate the position and the course of the vessels in vessel image 412. The left vessel segmentation data 461 indicate the position and the course of a catheter body 461a. The right vessel segmentation data 461 indicate the position of a catheter tip 461b.

Pathological vessel detection 480 detects pathological vessels in the contrasted vessel images. To this end, pathological vessel detection 480 performs image segmentation on the contrasted vessel images to identify areas within the contrasted vessel images that include pathological vessel segments. In one example, pathological vessel detection 480 may detect one or more pathological vessels based on any one of the image segmentation approaches trained on vessel images with annotated pathological vessels. The pathological vessels detected by pathological vessel detection 480 may then be included as pathological vessel data 515 in vessel roadmap 610.

Pathological conditions in vessels often affect the lumina of the vessel. Accordingly, pathological vessel detection 470 may in a further example detect pathological vessels based on their lumina. Accordingly, pathological vessel detection 470 may first determine centerlines of the vessels included in the contrasted vessel images. Then, pathological vessel detection 470 may determine, based on the centerlines, lumina of the vessels included in each vessel roadmap image of the vessel roadmap library. Finally, pathological vessel detection 470 may detect one or more pathological vessels based on the lumina of the vessels included in the contrasted vessel images.

A pathological vessel in the context of the present application may be any vessel experiencing a pathological condition, such as a stenosis, a lesion, a vasoconstriction or a vasodilation.

Pathological vessel detection 480 may further determine, e.g., based on the determined lumen of the pathological vessel, the grade of a pathological condition, e.g., a stenosis in a pathological vessel, as e.g., defined by the Society of Cardiovascular Computed Tomography (SCCT). Accordingly, pathological vessel detection 470 may based on a comparison of the total lumen with the unobstructed lumen, determine the grade of the stenosis. It will be understood that pathological vessel detection 470 may be able to also grade stenoses in vessels other than the coronary arteries based on the grading system applicable to such vessels.

In some cases, pathological vessel detection 480 may detect more than one pathological vessel. In such cases, pathological vessel detection 480 may further be able to determine in which order the pathological vessels may be treated during a medical intervention. Such a determination may for example be based on a starting position of a medical intervention and the position of the pathological vessel relative to the starting position or may be based on the grading of the severity of the pathological conditions of the pathological vessels discussed above.

It will be understood that pathological vessel detection 480 may also perform the detection based on input vessel image frames 412 directly or may be integrated with any one of the other processing entities of roadmap generation phase 400 performing image segmentation, i.e., contrast detection 440, vessel segmentation 450 and contrast application object segmentation 470.

Imaging physiological information 411 may be processed by cardiac cycle detection 420. Cardiac cycle detection 420 may identify one or more cardiac cycles within imaging physiological information 411. Cardiac cycle detection 120 may identify at least one cardiac cycle within imaging physiological information 411 by detecting a first R peak and a second R peak within imaging physiological information 411. The first and the second R peak may indicate the start and the end, respectively, of a cardiac cycle. It should be understood that any other graphical deflection of an ECG may be used to indicate the start and the end of a cardiac cycle. Accordingly, cardiac cycle detection 420 may e.g., detect a first and a second P wave. Cardiac cycle detection 420 may detect cardiac cycles using any suitable analysis of an ECG. For example, cardiac cycle detection 420 may detect cardiac cycles based on performing different types of analyses-based transforms, such as short-time Fourier-transform or based on deriving event vectors from the ECG and providing decision rules, which determine cardiac cycles based on the derived event vectors.

The one or more cardiac cycles detected by cardiac cycle detection 420 may be included in, e.g., stored as part of, first alignment data 412. In addition, the one or more cardiac cycles detected by cardiac cycle detection 420 may be provided to EDR detection 430.

EDR detection 430 may derive, based on the one or more cardiac cycles, an electrocardiogram derived respiratory (EDR) signal. The EDR signal may be derived by observing fluctuations between detected different cardiac cycles. Generally speaking, inhaling typically increases and exhaling typically decreases the heart rate. More precisely, such fluctuations can in some embodiments be used to derive the EDR signal by computing for the one or more detected cardiac cycles, the R-to-S peak. The R-to-S peak corresponds to the amplitude of the EDR signal. The R-to-S-peaks are then interpolated using cubic splines to obtain the EDR signal. It should be understood that in some embodiments, other approaches may be used to obtain an EDR signal from the imaging physiological information 411. The EDR signal may be included in, e.g., stored as part of, second alignment data 513.

It should be noted that in some embodiments, EDR detection 430 may be omitted. In such embodiments, second alignment data 513 may only include contrast application object segmentation data. Further, in some embodiments, EDR detection 430 may be included in cardiac cycle detection 420. For example, the approach used by cardiac cycle detection 420 to identify one or more cardiac cycles may also be able to directly provide an EDR signal or be able to provide an EDR signal based on an intermediate act of the approach.

Figure 6:
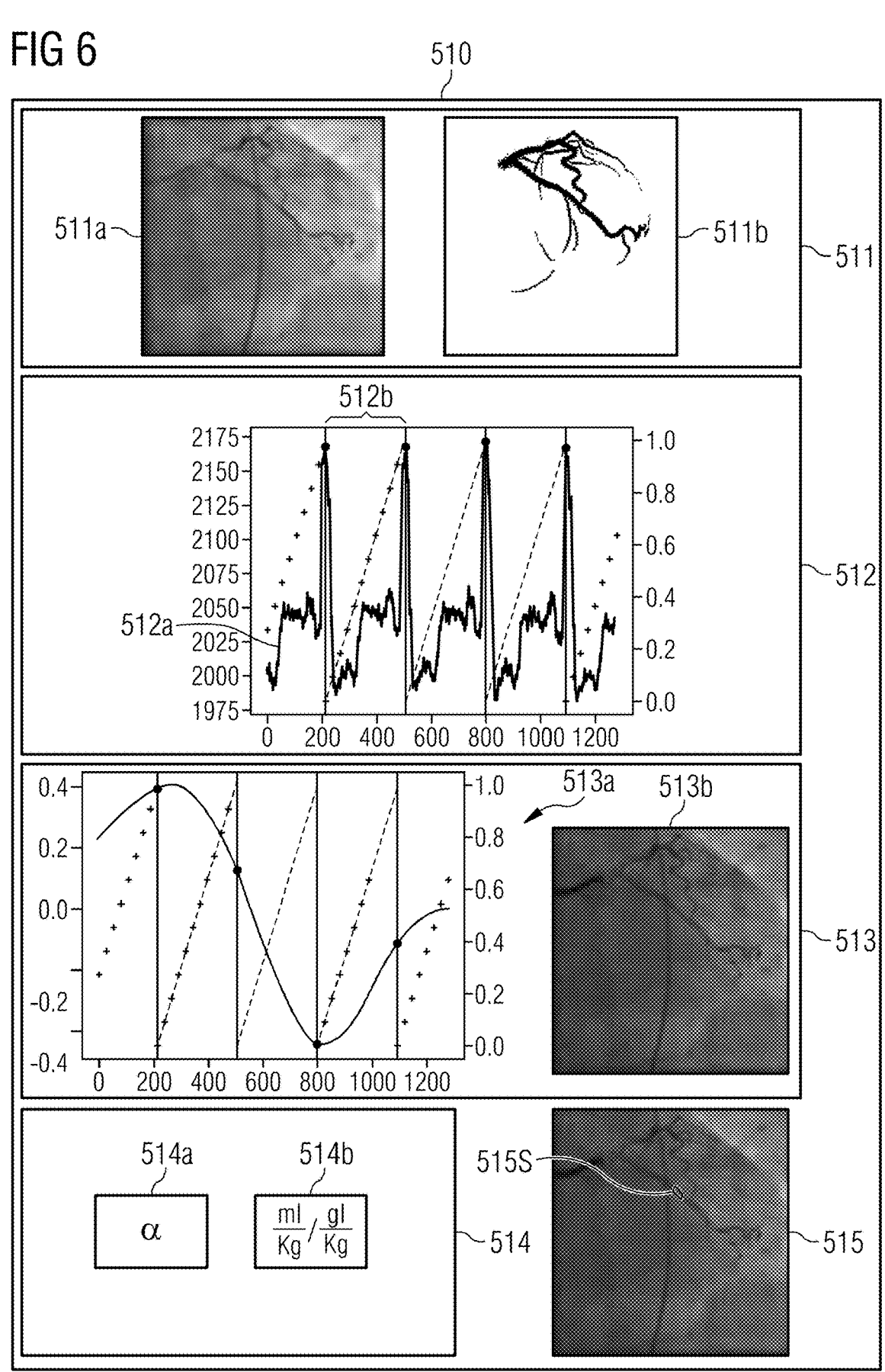
FIG. 6 shows an example of a vessel roadmap.

As mentioned above, the output of processing entities 420 to 470 forms part of vessel roadmaps 510, which are part of vessel roadmap library 700. To illustrate the data, which may be included in a vessel roadmap 510, FIG. 6 shows an example vessel roadmap 510, including a vessel roadmap image 511, first alignment data 512, second alignment data 513, imaging parameters 514 and pathological vessel information 515.

Vessel roadmap image 511 may include a vessel image 511*a*. Vessel roadmap image 511*a* corresponds to a vessel imaging frame generated by method 100, i.e., vessel imaging sequence generation 460, based on vessel input sequence 410. Further, vessel roadmap image 511 may include vessel segmentation data 511*b* generated by vessel segmentation 450. Both vessel roadmap 511*a* and vessel segmentation data 511*b* may be used as the roadmap to be laid over a fluoroscopy image during the roadmap deployment phase 600 by vessel overlay roadmap 691 discussed later. Accordingly, vessel roadmap image 511 is the part of vessel roadmap 511 providing the actual vessel roadmap. In some embodiments, vessel roadmap image 511 may correspond to a vessel image frame as generated by vessel image sequence 460 as well as an image indicating the vessel segmentation data generated by vessel imaging sequence generation 460 based on the vessel segmentation by vessel segmentation 450. In some embodiments, vessel roadmap image 511 may only include an image indicating the vessel segmentation data generated by vessel imaging sequence generation 460 based on the vessel segmentation by vessel segmentation 450, as illustrated by vessel segmentation data 511*b* in FIG. 6. In some embodiments, vessel roadmap image 511 may be data indicating the position of vessel pixels, which may subsequently be used to highlight corresponding pixels in a fluoroscopy image as vessel pixels.

First alignment data 512 may include imaging physiological information 411 as recorded as part of input vessel image sequence 410. Since imaging physiological information 411 may in some embodiments be an ECG, imaging physiological information 411 is shown in FIG. 6 as an alignment ECG 512*a*. Further, first alignment data 512 may include one or more cardiac cycles as detected by cardiac cycle detection 420. In FIG. 6, a cardiac cycle 512*b* is illustrated as indicted by adjacent R peaks in alignment ECG 512*a*. While first alignment data 512 of vessel roadmap 510 is shown here as based on an ECG curve, it should be understood that alignment ECG 512*a* and cardiac cycle 512*b* may typically be stored within second alignment data 512 as an indication of the ECG value, i.e., e.g., the amplitude of the complex lead discussed above, and the position of the ECG value within a cardiac cycle. Accordingly, the first alignment data may in some embodiments not include the entire alignment ECG 512*a*. Instead, first alignment data 512 may e.g., be a tuple with the first value indicating the amplitude and the second value indicating the position within a cardiac cycle. In some embodiments, if more than one cardiac cycle has been identified. Fist alignment data 512 may be a triple with the third value identifying the respective cardiac cycle. In some embodiments, in which cardiac cycle detection 420 is omitted, the cardiac cycle information may be replaced by temporal information indicating an associated point in time of the ECG value relative to other vessel roadmaps 510.

More generally, first alignment data 512 provide data to enable aligning vessel roadmap image 511 with a fluoroscopy image. Vessels shift for a variety of factors, including, but not limited to, cardiac muscle contraction and relaxation, i.e., cardiac motion, as well as breathing. First alignment data 512 enable compensation of vessel shift caused by cardiac motion. To this end, first alignment data 512 provide physiological information relating to the heart. It should therefore be understood that first alignment data 512 generally provide data enabling an alignment of a vessel roadmap with a fluoroscopy image necessitated due to vessel shifts caused by cardiac motion. First alignment data 512 may thus include any cardiac information necessary to compensate such vessel shifts.

Second alignment data 513 may include an EDR signal 513*a* generated by EDR detection 430, and contrast application object segmentation data 513*b* generated by contrast application object segmentation 440. EDR signal 513*a* is shown as a curve in FIG. 6 in order to illustrate EDR signal 513*a*. However, similarly to the discussion of alignment ECG 512*a*, EDR signal 513*a* may in some embodiments be a data set indicating the value of EDR signal 513*a* as well as the temporal position of the value within the EDR signal curve. Further, as shown in FIG. 6, contrast application object segmentation data 513*b* may in some embodiments be an image indicating the vessel segmentation data. In some embodiments, contrast application object segmentation data 513*b* may be data indicating the position of contrast application object pixels.

More generally, second alignment data 513 provide data to enable aligning vessel roadmap image 511 with a fluoroscopy image. While first alignment data 512 are described above as compensating vessel shift caused by cardiac motion, second alignment data 513 may compensate for vessel shift caused by breathing motion. To this end, second alignment data 513 provide both physiological information relating to the breathing and information relating to the position of the contrast application object, which may be shifted due to breathing. It should therefore be understood that second alignment data 513 generally provide data enabling an alignment of a vessel roadmap with a fluoroscopy image necessitated due to vessel shifts caused by breathing motion. Second alignment data 513 may thus include any breathing-related information necessary to compensate such vessel shifts. For example, in some embodiments, second alignment data 513 may include only one of EDR signal 513*a* and contrast application object segmentation data 513*b* since in some embodiments only one of the two may be sufficient to compensate vessel shifts cause by breathing motion. For example, in some embodiments EDR signal 513*a* may be omitted.

As discussed above, contrast application object segmentation data 513*b* is generated by contrast application object segmentation 470. Accordingly, second alignment data 513 is in some embodiments at least derived from vessel roadmap image 511. In embodiments, in which EDR signal 513*a* is also present, second alignment data 513 may further be derived from first alignment data 512 in addition to being derived from vessel image 511.

Imaging parameters 514 may include imaging parameters 413 associated with the imaging method used to obtain input vessel image frame 412 included as the vessel roadmap image 411. As shown in FIG. 6, imaging parameters 514 may thus include angiography angle 514*a* and contrast medium dosage 514*b*.

Pathological vessel information 515 is generated by pathological vessel detection 470. Accordingly, pathological vessel information 515 indicates pathological vessels in vessel roadmap 512. As illustrated in FIG. 6, pathological vessel information 515 may e.g., correspond to vessel roadmap 512 with a highlighted region 515S indicating a pathological vessel. In addition to or instead of, pathological vessel information 515 may in some embodiments include data identifying pixels in vessel roadmap 512, which are part of a pathological vessel segment. Generally speaking, pathological vessel information 515 may be any kind of information indicating which of the vessel visible in vessel roadmap 512 is a pathological vessel.

Vessel roadmap library 500 is the output generated by roadmap generation phase 400. This output may subsequently be deployed during roadmap deployment phase 600. In some embodiments, roadmap deployment phase 600 may be a medical intervention, such as a percutaneous coronary intervention (PCI). PCI is performed using fluoroscopy. Accordingly, vessel roadmap library 500 can be laid over the real-time fluoroscopy images during the PCI to guide a medical specialist through the coronary arteries to e.g., a stenosis without having to use a contrast medium. In such embodiments, roadmap generation phase 500 may include coronary angiography, which is used to obtain a coronary angiogram. The coronary angiogram in such embodiments corresponds to vessel image sequence 410. Since roadmap deployment phase 600 may be a medical intervention, it may also be referred to as an online phase, while roadmap generation phase 400 may also be referred to as an offline phase.

Roadmap deployment phase 600 performs real-time fluoroscopy 610 to obtain a real-time fluoroscopy image frames 611 and corresponding real-time first fluoroscopy information 612, real-time second fluoroscopy information 613 and imaging parameters 614.

Real-time fluoroscopy image frame 611 may be an image obtained using real-time fluoroscopy 610. During real-time fluoroscopy 610, no contrast medium needs to be injected into vessel or a vessel tree given that vessel image frames are provided by vessel roadmap library 500. Accordingly, since fluoroscopy is typically performed using X-ray, the only radio-opaque structure visible in the real-time fluoroscopy image frame 611, apart from e.g., bones of the patient, is a fluoroscopy object. Like input vessel image frame 412, real-time fluoroscopy image frame 611 may be stored as a DICOM image.

First fluoroscopy information 612 may be any kind of fluoroscopy physiological information of a patient on whom real-time fluoroscopy 610 is performed and which may be used to overlay and align vessel roadmaps 511 with fluoroscopy image 511. In some embodiments, first fluoroscopy information 612 may include an ECG recorded while real-time fluoroscopy 610 is performed. In such embodiments, first fluoroscopy information 612 may be processed by cardiac cycle detection 620 to identify one or more cardiac cycles based on the ECG. The identified one or more cardiac cycles may then also be included in the real-time fluoroscopy information 612. Cardiac cycle detection 620 may detect one or more cardiac cycles in the fluoroscopy ECG in the same manner as cardiac cycle detection 420 may detect one or more cardiac cycles in the ECG recorded while input vessel image sequence 410 is obtained.

The one or more cardiac cycles identified by cardiac cycle detection 620 may be processed by EDR detection 630. EDR detection 630 may derive an EDR signal based on the identified one or more cardiac cycles in the same manner as describe with respect to EDR detection 430. The derived EDR signal may then be included in second real-time fluoroscopy information 613.

As discussed above, in some embodiments, EDR detection 430 may be omitted. In such embodiments, EDR detection 630 may additionally derive an EDR signal based on the one or more cardiac cycles included in first alignment data 512 of a vessel roadmap 510 selected by roadmap selection 680, which will be discussed in more detail below. It should be noted that EDR detection 630 may also be omitted if EDR detection 430 is omitted. In such embodiments, vessel roadmap selection 680 and vessel roadmap alignment 692 may operate without any EDR signals.

In addition to the EDR signal, second real-time fluoroscopy information 613 may include fluoroscopy object segmentation data identifying a position of a fluoroscopy object in fluoroscopy image frame 611. The fluoroscopy object may be a fluoroscopy catheter, which may e.g., be used during a medical intervention, such as PCI. As opposed to the contrast application object, which may also be a catheter, the fluoroscopy catheter may typically not be used to inject contrast medium into a vessel, though it may still be configured for that purpose.

Imaging parameters 614 may indicate one or more parameters associated with an imaging method used to obtain real-time fluoroscopy image 811. Accordingly, imaging parameters 614 may correspond to imaging parameters 613 and may thus include at least one of a fluoroscopy angle and a contrast medium dosage.

Figure 7:
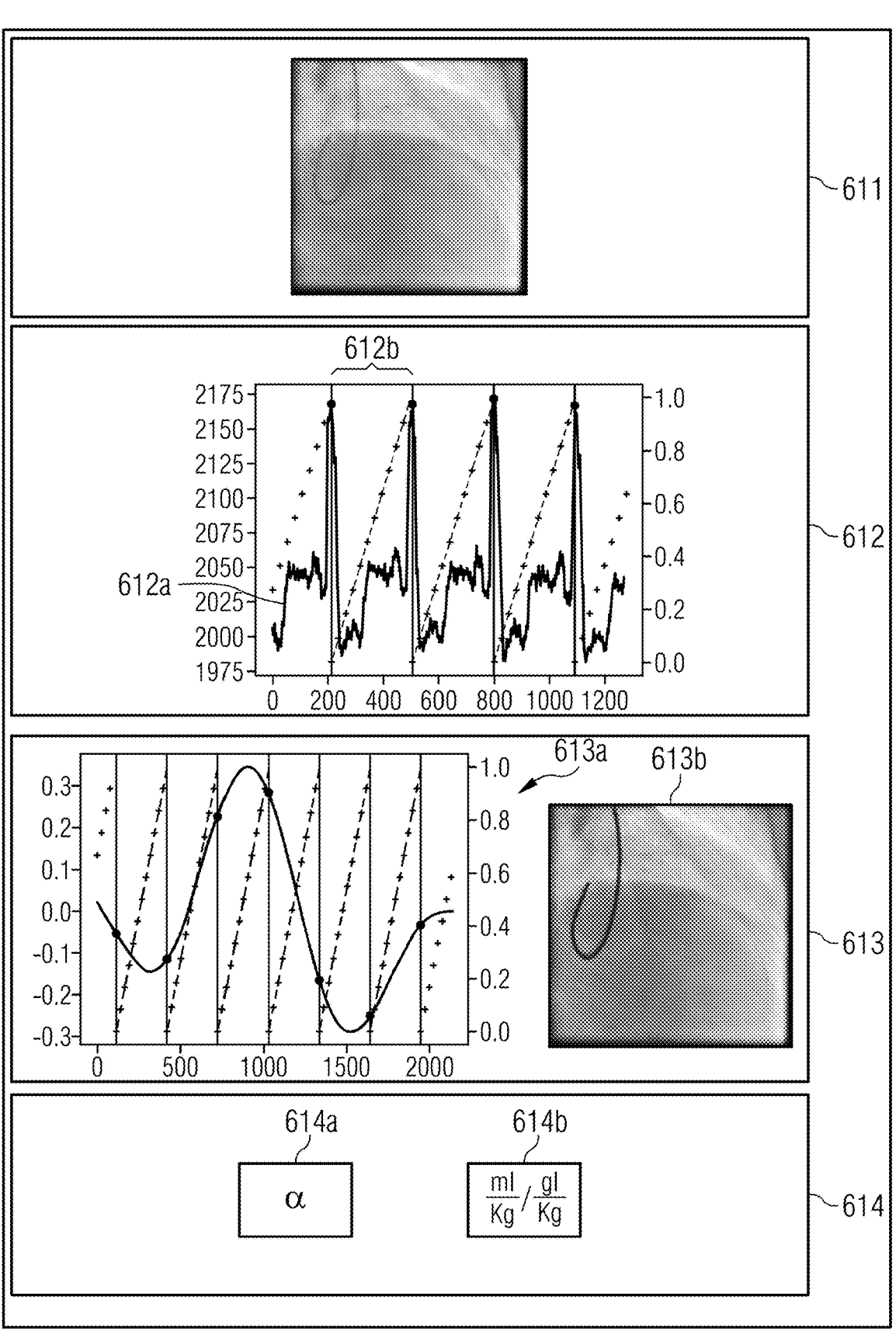
FIG. 7 shows an example of a real-time fluoroscopy image and information associated therewith.

The data recorded by real-time fluoroscopy 610 and processed by processing entities 620, 630 and 660 is illustrated in FIG. 7.

As shown in FIG. 7, real-time fluoroscopy image frame 611 includes the fluoroscopy image recorded by real time fluoroscopy 610. Typically, only the fluoroscopy object is visible in real-time fluoroscopy image frame 611, unless other radio-opaque structures of the patient are visible.

First fluoroscopy information 612 includes fluoroscopy ECG 612a recorded during real-time fluoroscopy and one or more cardiac cycles 612b identified by cardiac cycle detection 620. Analogously to first alignment data 512, first fluoroscopy information 612 may include any cardiac information necessary to compensate vessel shifts when laying one of the vessel roadmap images 511 over real-time fluoroscopy image frame 611. Accordingly, in some embodiments, first fluoroscopy information 612 may only include fluoroscopy ECG 612a or may include other or additional information to compensate vessel shifts when laying one of the vessel roadmap images 511 over real-time fluoroscopy image frame 611. Further, while fluoroscopy ECG 612a is illustrated as the ECG curve recorded during real-time fluoroscopy 610, in some embodiments only values corresponding to the point on the ECG curve may be included in first real-time fluoroscopy information 612, e.g., a tuple or a triple, respectively, including the amplitude value of the complex lead of the fluoroscopy ECG 612a, the temporal position within the ECG and an indication of the identified cardiac cycle.

Second real-time fluoroscopy information 613 may include a fluoroscopy EDR signal 613a generated by EDR detection 630 and contrast application object segmentation data 813b generated by contrast application object segmentation 860. EDR signal 613a is shown as a curve in FIG. 7 to illustrate fluoroscopy EDR signal 613a. However, similarly to the discussion of preceding discussions of curves, i.e., alignment ECG 512a, EDR signal 513a and fluoroscopy ECG 612a, fluoroscopy EDR signal 613a may in some embodiments be a data set indicating the value of fluoroscopy EDR signal 613a as well as the temporal position of the value within the fluoroscopy EDR signal curve. Further, as shown in FIG. 7, fluoroscopy object segmentation data 613b may in some embodiments be an image indicating the vessel segmentation data. In some embodiments, fluoroscopy object segmentation data 613b may be data indicating the position of fluoroscopy object pixels.

Real-time fluoroscopy image frames 611 are processed by fluoroscopy imaging sequence generation 670, which generates a fluoroscopic image sequence based on Real-time fluoroscopy image frames 611 according to method 100 of FIG. 1.

The fluoroscopic image sequence generated by fluoroscopy imaging sequence generation 670 and vessel roadmap library 500 may be provided to a vessel roadmap selection 690. Vessel roadmap selection 690 may select one of the vessel roadmaps 510 from roadmap library 500 based on comparing first real-time fluoroscopy information 612 with first alignment data 512 of each vessel roadmap 510 in roadmap library 500.

More precisely, vessel roadmap selection 680 may compare alignment ECG 512a of each vessel roadmap 510 with fluoroscopy ECG 612a to determine a vessel roadmap 510 approximately corresponding, in terms of the respective alignment ECG 512a, to fluoroscopy ECG 612a. By selecting a vessel roadmap based on an ECG comparison, a vessel roadmap 510 can be chosen in which the position of the vessels is most similar, due to a similar shift caused by similar cardiac motion, to the position of the vessels in real time fluoroscopy image 611.

In addition, in some embodiments, vessel roadmap selection 670 may select a vessel roadmap 510 from roadmap library 500 based on comparing second real-time fluoroscopy information 613 with the second alignment data 513 of each vessel roadmap 510. More precisely, vessel roadmap selection 870 may additionally compare EDR signal 513a of each vessel roadmap 510 with fluoroscopy EDR signal 513a to determine a vessel roadmap 510 approximately corresponding, in terms of the respective EDR signal 513a, to fluoroscopy EDR signal 613a. By selecting a vessel roadmap additionally based on an EDR signal comparison, a vessel roadmap 510 can be chosen in which the position of the vessels is most similar, due to a similar shift caused by similar breathing motion, to the position of the vessels in real time fluoroscopy image 611.

In summary, vessel roadmap selection 670 may based on an ECG comparison and in some embodiments based on an additional EDR comparison, select a vessel roadmap 510 from vessel roadmap library 500. The vessels visible in the accordingly selected vessel roadmap 510 have experienced a similar shift due to cardiac motion as well as due to breathing motion. The position of the vessels visible in the accordingly selected vessel roadmap 510 may thus be approximately similar to the position of the vessels in real-time fluoroscopy image 611.

Angle comparison 690 may compare the angiography angle included in the imaging parameters 514 of vessel roadmap 510 with the fluoroscopy angle included in imaging parameters 614 of real-time fluoroscopy 610. The comparison performed by angle comparison 680 may ensure that the view provided by selected vessel roadmap image 511 and the view provided by real-time fluoroscopy image 611 are obtained at approximately the same C-arm position. If the angiography angle and the fluoroscopy angle are approximately the same, the views provided by selected vessel roadmap image 511 and real-time fluoroscopy image 611 are approximately similar. If the angiography angle and the fluoroscopy angle differ, e.g., differ by more than an angle difference threshold, the views provided by selected vessel roadmap image 511 and real-time fluoroscopy image 611 may be too different. Accordingly, in such cases, angle comparison 690 may decide to refrain from overlaying vessel roadmap image 511 over real-time fluoroscopy image 611. Due the deviation of the views in 3D corresponding to the difference of the angles, vessel roadmap overlay 691 and vessel roadmap alignment 692 may not be able properly overlay and align the views. The angle difference threshold may e.g., be 5° or 2°.

Angle comparison 690 may in some embodiments indicate, via a display, such as display 1060, to a medical specialist operating a medical imaging device, such as medical imaging device 1000, that the angiography angle and the fluoroscopy angle differ. Angle comparison 690 may further indicate how to correct the fluoroscopy angle by indicating the proper angular position to which C-arm 1030 of medical imaging device 1200 should be moved. In some embodiments, angle comparison 680 may also be configured to control C-arm 1030 and may thus be configured to move C-arm 1030 to the proper angular position.

Vessel roadmap overlay 691 may lay the selected vessel roadmap image 511 of the selected vessel roadmap 510 over the fluoroscopic image sequence generated by fluoroscopy imaging sequence generator 670. In some embodiments, vessel roadmap overlay 691 may perform the overlay by superimposing vessel image 511a over the fluoroscopic image sequence generated by fluoroscopy imaging sequence generator 670. Superimposing vessel image 511a may in some embodiments be achieved by transparent color blending, i.e., two pixel values from vessel image 511a, one corresponding to the pixel value as recorded originally in corresponding vessel image 512 and one corresponding to a color selected for vessel representation, can be simultaneously shown. In some embodiments, vessel roadmap image 511a may be overlaid with a variable level of opacity. In some embodiments, vessel segmentation data 511b may be integrated into the fluoroscopic image sequence generated by fluoroscopy imaging sequence generator 670, e.g., by changing the values of the pixels indicated as vessel pixels by vessel segmentation data 511b.

Figure 8:
FIG. 8 shows examples of laying a vessel roadmap over a real-time fluoroscopy.
Figure 8:
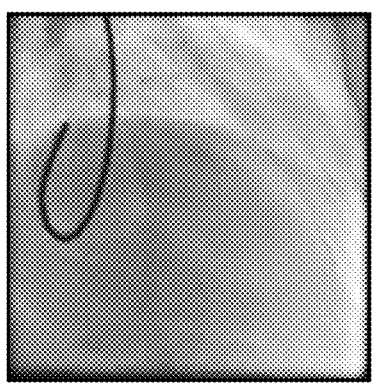
Figure 8:
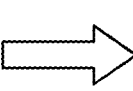
Figure 8:
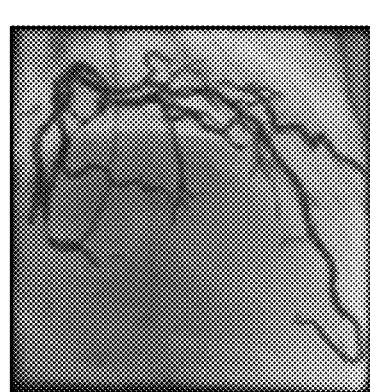

FIG. 8 provides an example of vessel roadmap overlay 691. On the left, a frame the fluoroscopic image sequence generated by fluoroscopy imaging sequence generator 670 with a visible fluoroscopy object can be seen prior to the overlay of a vessel roadmap image 511. On the right, the frame can be seen after the overlay of a vessel roadmap image 511.

Roadmap image 511 laid over the frame of the fluoroscopic image sequence generated by fluoroscopy imaging sequence generator 670 by vessel roadmap overlay 691 may be aligned by vessel roadmap alignment 692. Vessel roadmap alignment 692 aligns overlaid vessel roadmap image 511 and the frame of the fluoroscopic image sequence generated by fluoroscopy imaging sequence generator 670 based on second alignment data 513 and real time second fluoroscopy information 813. In particular, vessel roadmap alignment 892 aligns the position of the contrast application object with the position of the fluoroscopy object based on contrast application object segmentation data 513b and fluoroscopy object segmentation data 613b. In other words, vessel roadmap alignment 692 aligns the positions of the contrast application object and the fluoroscopy object, which may both be catheters. For example, both object segmentation data 513b and fluoroscopy object segmentation data 613b may each indicate, in some embodiments, a centerline of the respective catheter. In such embodiments, vessel roadmap alignment 692 aligns vessel roadmap 510 with real-time the frame of the fluoroscopic image sequence generated by fluoroscopy imaging sequence generator 670 by minimizing the sum of squared distances between closest points on the centerlines of the catheters. It should be noted that aligning may include in-plane rotation, i.e., rotating the roadmap to achieve better alignment. By aligning the positions of the contrast application object with the position of the fluoroscopy object, any vessel shift caused by breathing motion may be further compensated in order to further improve the accuracy of overlaid vessel roadmap 510.

Figure 9:
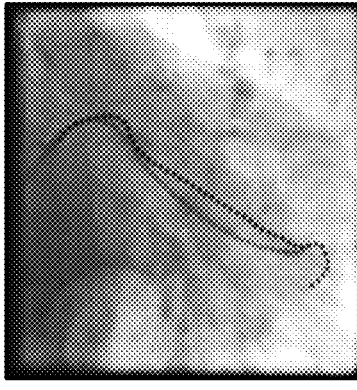
FIG. 9 shows an example of overlaying a vessel roadmap and a real-time fluoroscopy image.
Figure 9:
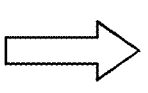
Figure 9:
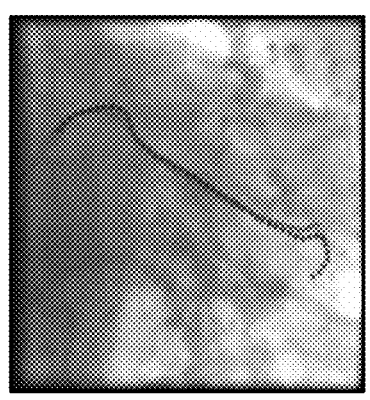

FIG. 9 provides an example of an alignment by vessel roadmap alignment 692 based on catheter centerlines. As can be seen on the left side of FIG. 9, prior to alignment by vessel roadmap alignment 692, the centerlines are apart from one another. After alignment by vessel roadmap alignment 692, the centerlines are approximately in the same position.

Finally, pathological vessel guidance 693 may provide guidance for the fluoroscopy object to the pathological vessel detected by pathological vessel detection 480 based on the selected vessel roadmap 511 and second fluoroscopy information 613. To this end, pathological vessel guidance 693 may determine a path from the fluoroscopy object to the pathological vessel based on the second real-time fluoroscopy information 613, which includes the fluoroscopy segmentation data, and the vessel segmentation data 511$b$ included in the selected vessel roadmap image 511. In other words, the path may indicate the vessel segments the fluoroscopy object needs to pass through to reach the pathological vessel from the current position of the fluoroscopy object within the vessels of a patient. Accordingly, pathological vessel guidance 883 may provide guidance for the fluoroscopy object by indicating the vessel segments through which the fluoroscopy object needs to pass to reach the pathological vessel.

Pathological vessel guidance 693 may in some embodiments, provide the guidance to a medical specialist operating the fluoroscopy object e.g., by displaying the path determined by pathological vessel guidance 693 on a display, such as display 1060, to the medical specialist. In some embodiments, the fluoroscopy object may be a robot-controlled fluoroscopy object. In such embodiments, pathological vessel guidance 393 may provide the guidance to the robot-controlled fluoroscopy object to enable the robot-controlled fluoroscopy object to be guided to the pathological vessel.

In summary, vessel roadmap selection 680, vessel roadmap overlay 691 and vessel roadmap alignment 692 select, overlay and align one of the vessel roadmaps 510 with the frame of the fluoroscopic image sequence generated by fluoroscopy imaging sequence generator 670 in order to provide a vessel roadmap during roadmap deployment phase 600. By taking into account first alignment data 512, second alignment data 513, the first fluoroscopy information 612 and the second fluoroscopy information 613, a vessel roadmap can be selected, overlaid and aligned with the frame of the fluoroscopic image sequence generated by fluoroscopy imaging sequence generator 670, which corresponds to the actual position of the vessels in the frame of the fluoroscopic image sequence generated by fluoroscopy imaging sequence generator 670 without having to inject contrast medium. Thus, vessel roadmap selection 680, vessel roadmap overlay 691 and vessel roadmap alignment 692 compensate any motion of the vessels, such as cardiac motion or breathing motion, to correctly overlay one of the vessel roadmaps 510 over fluoroscopy image 611. Further, the duration of the fluoroscopy may be reduced based on generated vessel roadmap library 500, thereby reducing radiation exposure due to the guidance provided by pathological vessel guidance 893, which provides direct guidance from the position of the fluoroscopy objection to the pathological vessel. This guidance reduces the durations of medical interventions, such as PCI, since guidance based on the properly selected, overlaid and aligned roadmap may enable fast and reliable navigation with the fluoroscopy object through the vessels.

As briefly discussed above, FIGS. 10A and 10B show an exemplary medical imaging system 1000, which may e.g., be used to obtain the input vessel imaging sequence. Medical imaging system 1000 may be used for both angiography and fluoroscopy. However, angiography and fluoroscopy may also be performed on separate systems with largely identical elements. In FIG. 10A, medical imaging system 1000 is in neutral position $P_0$. In FIG. 10B, medical imaging system 1000 is in a rotated position $P_1$. As discussed above, the angle between the two positions is referred to as the angiography angle or the fluoroscopy angle, depending on the imaging process currently performed by medical imaging system 1000. Medical imaging system 1000 includes C-arm 1030, on which X-ray emitter 1031 and X-ray detector 1032 may be mounted. C-arm 1030 and thereby X-ray emitter 1031 and X-ray detector 1032 are positioned to center around patient surface 1040. X-ray emitter 1031 may emit X-rays which may penetrate through a patient positioned on patient surface 1040. X-ray detector 1032 detects the X-rays emitted from X-ray emitter 1031. When a patient-on-patient surface 1040 is injected with a radio-opaque contrast agent into the patient's vessels, some of the X-rays emitted by X-ray emitter 1031 are absorbed by the radio-opaque contrast agent, leading X-ray detector 1032 to detect an image of the vessels filled with the radio-opaque contrast agent, i.e., an angiogram. X-ray emitter 1031 and X-ray detector 1032 may also collectively be referred to as x-ray imaging means.

C-arm 1030 may be coupled to C-arm rotation unit (motor) 1020. C-arm rotation unit 1020 may be any motorized mechanism configured to rotate C-arm 1030 according to an angiography angel or a fluoroscopy angle as either instructed by the medical specialist or angle comparison 690. C-arm rotation unit 1020 may be attached to and controlled by C-arm control unit (controller) 1010. C-arm control unit 1010 may be any kind of circuitry capable of controlling C-arm 1030. For example, C-arm control unit 1010 may include computing device (computer) 1100 of FIG. 11 or may be configured to interface with computing device 1100.

Medical imaging system 1000 may further include a control panel 1050 mounted onto a side surface of patient surface support 1041. Control panel 1050 may be used to control C-arm 1030 in embodiments in which method 400 displays real-time fluoroscopy image 1011 with an overlaid vessel roadmap image 211 including the path to the one or more pathological vessels to the medical specialist in order to guide the medical specialist to the one or more pathological vessels. FIG. 10 does not show any connections between control panel 1050 and C-arm 1030 to simplify the depiction of exemplary medical imaging system 1000. In some embodiments, the connection may be wireless. In some embodiments, the connection may be wired and may e.g., be integrated into the ceiling of the room where medical imaging system 1000 is located.

Medical imaging system 1000 may finally also include a display 1060. Display 1060 may be used to display information to the medical specialist, such as the vessel imaging sequence generated by method 100 with an overlaid vessel roadmap image 511 including the path to the one or more pathological vessels. Further, display 1060 may be used to display the vessel segmentation data included in overlaid vessel roadmap image 511, including labels for the various vessel segments visible on display 1060. In some embodiments, display 1060 may 1060 be a touch screen, which may be used to toggle the display of the vessel segmentation data on and off. In some embodiments, display 1060 may further display a confidence level indicating the confidence of roadmap selection 680, vessel comparison 691 and vessel roadmap alignment 692 in the accuracy of the overly and the alignment. In some embodiments, display 1060 may also display, to the medical specialist, the appropriate angular position of C-arm 1030 during fluoroscopy to enable proper overlay and alignment of vessel roadmap image 511 as determined by angle comparison 690.

FIG. 11 shows a computing device 1100 configured to perform method 100 of FIG. 1 and/or the workflow of FIGS. 4A and 4B. Computing device 1100 may 1100 may include a processor 1110, a graphics processing unit (GPU) 1120, a memory 1130, a bus 1140, a storage 1350, a removable storage 1160, an medical imaging system control interface 1170 and a communications interface 1180.

Processor 1110 may be any kind of single-core or multi-core processing unit employing a reduced instruction set (RISC) or a complex instruction set (CISC). Exemplary RISC processing units include ARM based cores or RISC V based cores. Exemplary CISC processing units include x86 based cores or x86-64 based cores. Processor 1310 may further be an application specific integrated circuit (ASIC) or a field-programmable gate-array specially tailored to or programmed, respectively, to perform method 100 and/or the workflow of FIGS. 4A and 4B. Processor 1110 may perform instructions causing computing device 1100 to perform method 100 and/or the workflow of FIGS. 4A and 4B. Processor 1110 may be directly coupled to any of the components of computing device 1100 or may be directly coupled to memory 1130, GPU 1320 and bus 1140.

GPU 1120 may be any kind of processing unit optimized for processing graphics related instructions or more generally for parallel processing of instructions. As such, GPU 1120 may perform part or all of method 100 and/or the workflow of FIGS. 4A and 4B to enable fast parallel processing of instructions relating to method 100 and/or the workflow of FIGS. 4A and 4B. It should be noted that in some embodiments, processor 1110 may determine that GPU 1120 need not perform instructions relating to method 1100. GPU 1120 may be directly coupled to any of the components of computing device 1100 or may be directly coupled to processor 1110 and memory 1130. GPU 1120 may also be coupled to a display, such as display 1060 of medical imaging system 1000, via connection 1120C. In some embodiments, GPU 1120 may also be coupled to bus 1140.

Memory 1130 may be any kind of fast storage enabling processor 1110 and GPU 1120 to store instructions for fast retrieval during processing of the instructions well as to cache and buffer data. Memory 1130 may be a unified memory coupled to both processor 1110 and GPU 1120 enabling allocation of memory 1130 to processor 1310 and GPU 1320 as needed. Alternatively, processor 1310 and GPU 1120 may be coupled to separate processor memory 1130a and GPU memory 1130b.

Storage 1150 may be a storage device enabling storage of program instructions and other data. For example, storage 1150 may be a hard disk drive (HDD), a solid-state disk (SSD) or some other type of non-volatile (non-transitory) memory. Storage 1150 may for example store the instructions of method 100 and/or the workflow of FIGS. 4A and 4B as well as the e.g., the input vessel imaging sequence, the vessel imaging sequence and vessel roadmap library 500.

Removable storage 1160 may be a non-transitory storage device which can be removably coupled with computing device 1100. Examples include a digital versatile disc (DVD), a compact disc (CD), a Universal Serial Bus (USB)

storage device, such as an external SSD, or a magnetic tape. Removable storage 1140 may for example be used to provide the input vessel imaging sequence to computing device 1100 and thereby to method 100 or to store the vessel imaging sequence generated by method 100. It should be noted that removable storage 1160 may also store other data, such as instructions of method 100, or may be omitted.

Storage 1150 and removable storage 1160 may be coupled to processor 1110 via bus 1140. Bus 1140 may be any kind of bus system enabling processor 1110 and optionally GPU 1120 to communicate with storage device 1150 and removable storage 960. Bus 1140 may for example be a Peripheral Component Interconnect express (PCIe) bus or a Serial AT Attachment (SATA) bus.

Medical imaging system control interface 1170 may enable computing device 1100 to interface with medical imaging system 1000 via connection 1170C to control C-arm 1030 in accordance with the workflow of FIGS. 4A and 4B. For example, medical imaging system control interface 1170 may be dedicated logic circuitry configured to control rotation of C-arm 1030. In some embodiments, medical imaging system control interface 1170 may be C-arm control unit 1110. In some embodiments, medical imaging system control interface 1170 may also be omitted and computing device 1100 interfaces with medical imaging system 1000 solely via communications interface 1180. In such embodiments, processor 1110 may control C-arm directly via communications interface 1170. Medical imaging system control interface 1170 may further be coupled to a robot-controlled fluoroscopy object, e.g., a catheter, in order to guide the robot-controlled fluoroscopy object to the one or more pathological vessels.

Communications interface 1180 may enable computing device 1100 to interface with external devices, either directly or via network, via connection 1180C. Communications interface 1180 may for example enable computing device 1100 to couple to a wired or wireless network, such as Ethernet, Wifi, a Controller Area Network (CAN) bus or any bus system appropriate in medical systems. For example, computing device 1100 may be coupled with medical imaging system 1000 via connection 1180C to receive the input vessel imaging sequence or to provide, overlay and align a selected vessel roadmap image 511. Communications interface may also be a USB port or a serial port to enable direct communication with an external device.

As stated above, computing device 1100 may be integrated with medical imaging system 1000. For example, computing device 1100 may be integrated with C-arm control unit 1030 or may be placed inside patient surface support 1040.

The invention may further be illustrated by the following examples.

In an example, a method for generating a vessel imaging sequence including a plurality of vessel imaging frames and a corresponding electrocardiogram (ECG) signal, including obtaining an input vessel imaging sequence including a plurality of input vessel imaging frames and a corresponding input ECG signal, encoding, using a first encoder, the input vessel imaging sequence to generate a plurality of vessel latent space vectors, each vessel latent space vector corresponding to an input vessel imaging frame of the input vessel imaging sequence, encoding, using a second encoder, the input ECG signal to generate a plurality of ECG latent space vectors, decoding, using a first decoder, the plurality of vessel latent space vectors and the plurality of ECG latent space vectors to generate the vessel imaging sequence and decoding, using a second decoder, the vessel latent space vector and the ECG latent space vector to generate the ECG signal.

In an example, a frame rate of the input vessel imaging sequence may be lower than a frame rate of the vessel imaging sequence.

In an example, the input vessel imaging sequence may be one of an input vessel image sequence, an input vessel segmentation sequence derived from the input vessel image sequence and an input fluoroscopic imaging sequence.

In an example, the input vessel imaging sequence may be obtained during a single cardiac cycle.

In an example, obtaining the input vessel imaging sequence and the corresponding input ECG signal may include deriving the input ECG signal from the input vessel imaging sequence.

In an example, the method may further include deriving at least one of a respiratory motion model and a cardiac motion model from the plurality of vessel latent space vectors and the plurality of ECG latent space vectors.

In an example, the plurality of vessel latent space vectors and the plurality of ECG latent space vectors may respectively be configured to enable a reconstruction of the input vessel imaging sequence and of the input ECG signal.

In an example, the first encoder, the second encoder, the first decoder and the second decoder may be one of a convolutional neural network, a principal component analysis and a transformer-based neural network architecture.

In an example, the first encoder and the first decoder may form a first modified latent space autoencoder and the second encoder and the second decoder may form a second modified latent space autoencoder.

In an example, a vessel imaging sequence generation device, the vessel imaging sequence including a plurality of vessel imaging frames, includes at least one processor; and a storage medium including machine-readable instructions, wherein the machine-readable instructions cause the at least one processor to obtain an input vessel imaging sequence including a plurality of input vessel imaging frames and a corresponding input ECG signal, encode, using a first encoder, the input vessel imaging sequence to generate a plurality of vessel latent space vectors, each vessel latent space vector corresponding to an input vessel imaging of the input vessel imaging sequence, encode, using a second encoder, the ECG signal to generate a plurality of ECG latent space vectors, decode, using a first decoder, the plurality of vessel latent space vectors and the plurality of ECG latent space vectors to generate the vessel imaging sequence and decode, using a second decoder, the vessel latent space vector and the ECG latent space vector to generate the ECG signal.

In an example, a frame rate of the input vessel imaging sequence may be lower than a frame rate of the vessel imaging sequence.

In an example, the input vessel imaging sequence may be one of an angiographic imaging sequence, a vessel segmentation sequence derived from the angiographic imaging sequence and a fluoroscopic imaging sequence.

In an example, the input vessel imaging sequence may be obtained during a single cardiac cycle.

In an example, to obtain the input vessel imaging sequence and the corresponding input ECG signal, the machine-readable instructions may further cause the at least one processor to derive the input ECG signal from the input vessel imaging sequence.

In an example, the machine-readable instructions may further cause the at least one processor to derive at least one of a respiratory motion model and a cardiac motion model from the plurality of vessel latent space vectors and the plurality of ECG latent space vectors.

The preceding description has been provided to illustrate the generation of vessel imaging sequences and the use thereof in a vessel imaging workflow. It should be understood that the preceding description is in no way meant to limit the scope of the invention to the precise embodiments discussed throughout the description. Rather, the person skilled in the art will be aware that these embodiments may be combined, modified or condensed without departing from the scope of the invention as defined by the following claims.

The invention claimed is:

1. A method for generating a vessel imaging sequence comprising a plurality of vessel imaging frames and a corresponding electrocardiogram (ECG) signal, the method comprising:

obtaining an input vessel imaging sequence comprising a plurality of input vessel imaging frames and a corresponding input ECG signal;

encoding, using a first encoder, the input vessel imaging sequence, the encoding using the first encoder generating a plurality of vessel latent space vectors, each vessel latent space vector corresponding to an input vessel imaging frame of the input vessel imaging sequence;

encoding, using a second encoder, the input ECG signal, the encoding using the second encoder generating a plurality of ECG latent space vectors;

decoding, using a first decoder, the plurality of vessel latent space vectors and the plurality of ECG latent space vectors, the decoding using the first decoder generating the vessel imaging sequence; and decoding, using a second decoder, the vessel latent space vector and the ECG latent space vector, the decoding using the second decoder generating the ECG signal.

2. The method of claim 1, wherein a frame rate of the input vessel imaging sequence is lower than a frame rate of the vessel imaging sequence.

3. The method of claim 2, wherein the input vessel imaging sequence is obtained during a single cardiac cycle.

4. The method of claim 3, wherein the first encoder, the second encoder, the first decoder and the second decoder are each a convolutional neural network, a principal component analysis or a transformer-based neural network architecture.

5. The method of claim 4, wherein:

the first encoder and the first decoder form a first modified latent space autoencoder; and the second encoder and the second decoder form a second modified latent space autoencoder.

6. The method of claim 1, wherein the input vessel imaging sequence is an input vessel image sequence, an input vessel segmentation sequence derived from the input vessel image sequence, or an input fluoroscopic imaging sequence.

7. The method of claim 1, wherein the input vessel imaging sequence is obtained during a single cardiac cycle.

8. The method of claim 1, wherein the obtaining the input vessel imaging sequence and the corresponding input ECG signal includes deriving the input ECG signal from the input vessel imaging sequence.

9. The method of claim 1, further comprising deriving at least one of a respiratory motion model and a cardiac motion model from the plurality of vessel latent space vectors and the plurality of ECG latent space vectors.

10. The method of claim 1, wherein the plurality of vessel latent space vectors and the plurality of ECG latent space vectors are respectively configured to enable a reconstruction of the input vessel imaging sequence and of the input ECG signal.

11. The method of claim 1, wherein the first encoder, the second encoder, the first decoder and the second decoder are each a convolutional neural network, a principal component analysis, or a transformer-based neural network architecture.

12. The method of claim 1, wherein:

the first encoder and the first decoder form a first modified latent space autoencoder; and the second encoder and the second decoder form a second modified latent space autoencoder.

13. A vessel imaging sequence generation system, the vessel imaging sequence including a plurality of vessel imaging frames, the vessel imaging sequence generation system comprising:

at least one processor; and a storage medium comprising machine-readable instructions, wherein the machine-readable instructions cause the at least one processor to:

obtain an input vessel imaging sequence comprising a plurality of input vessel imaging frames and a corresponding input ECG signal;

encode, using a first encoder, the input vessel imaging sequence to generate a plurality of vessel latent space vectors, each vessel latent space vector corresponding to an input vessel imaging of the input imaging sequence;

encode, using a second encoder, the ECG signal to generate a plurality of ECG latent space vectors;

decode, using a first decoder, the plurality of vessel latent space vectors and the plurality of ECG latent space vectors to generate the vessel imaging sequence; and decode, using a second decoder, the vessel latent space vector and the ECG latent space vector to generate the ECG signal.

14. The vessel imaging sequence generation system of claim 13, wherein a frame rate of the input vessel imaging sequence is lower than a frame rate of the vessel imaging sequence.

15. The vessel imaging sequence generation system of claim 14, wherein the input vessel imaging sequence is obtained during a single cardiac cycle.

16. The vessel imaging sequence generation system of claim 15, wherein the machine-readable instructions further cause the at least one processor to derive at least one of a respiratory motion model and a cardiac motion model from the plurality of vessel latent space vectors and the plurality of ECG latent space vectors.

17. The vessel imaging sequence generation system of claim 13, wherein the input vessel imaging sequence is an angiographic imaging sequence, a vessel segmentation sequence derived from the angiographic imaging sequence, or a fluoroscopic imaging sequence.

18. The vessel imaging sequence generation system of claim 13, wherein the input vessel imaging sequence is obtained during a single cardiac cycle.

19. The vessel imaging sequence generation system of claim 13, wherein, to obtain the input vessel imaging sequence and the corresponding input ECG signal, the machine-readable instructions further cause the at least one processor to derive the input ECG signal from the input vessel imaging sequence.

20. The vessel imaging sequence generation system of claim 13, wherein the machine-readable instructions further cause the at least one processor to derive at least one of a respiratory motion model and a cardiac motion model from the plurality of vessel latent space vectors and the plurality of ECG latent space vectors.

* * * * *